United States Patent
Dehmlow et al.

(10) Patent No.: US 7,253,282 B2
(45) Date of Patent: Aug. 7, 2007

(54) HEXAFLUOROISOPROPANOL SUBSTITUTED CYCLOHEXANE DERIVATIVES

(75) Inventors: Henrietta Dehmlow, Grenzach-Wyhlen (DE); Bernd Kuhn, Liestal (CH); Raffaello Masciadri, Basel (CH); Narendra Panday, Basel (CH); Hasane Ratni, Habsheim (FR); Matthew Blake Wright, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 31 days.

(21) Appl. No.: 11/303,119

(22) Filed: Dec. 16, 2005

(65) Prior Publication Data

US 2006/0135601 A1 Jun. 22, 2006

(30) Foreign Application Priority Data

Dec. 22, 2004 (EP) .................... 04106896

(51) Int. Cl.

| | |
|---|---|
| C07C 311/12 | (2006.01) |
| C07C 311/13 | (2006.01) |
| C07C 223/23 | (2006.01) |
| A61K 31/325 | (2006.01) |
| A61K 31/215 | (2006.01) |
| A61K 31/22 | (2006.01) |

(52) U.S. Cl. .................... 546/80; 564/192; 564/182; 560/132; 560/129; 514/601; 514/663; 514/571

(58) Field of Classification Search .............. 564/80, 564/192, 182; 560/132, 129; 514/601, 663, 514/571

See application file for complete search history.

(56) References Cited

FOREIGN PATENT DOCUMENTS

| | | | |
|---|---|---|---|
| WO | WO 02/058690 A2 | 8/2002 | |
| WO | WO 03/090732 A1 | 11/2003 | |
| WO | WO 03/099769 | 12/2003 | |

OTHER PUBLICATIONS

Willy et al., Genes Dev. 1995, 9:1033-45.
Song et al., Proc Natl Acad Sci USA. 1994, 91:10809-13.
Miller NE., Lipids 1978, 13:914-9.
Gordon et al., Am J Med. 1977, 62:707-14.
Lund et al., Arterioscler. Thromb. Vasc. Biol. 2003, 23:1169-77.
Joseph and Tontonoz, Curr. Opin. Pharmacol. 2003, 3:192-7.
Cao et al., J Biol Chem. 2003, 278:1131-6.

*Primary Examiner*—Joseph K. McKane
*Assistant Examiner*—Michael P. Barker
(74) *Attorney, Agent, or Firm*—George W. Johnston; Dennis P. Tramaloni; Samuel H. Megerditchian

(57) ABSTRACT

The invention is concerned with novel hexafluoroisopropanol substituted cyclohexane derivatives of formula (I)

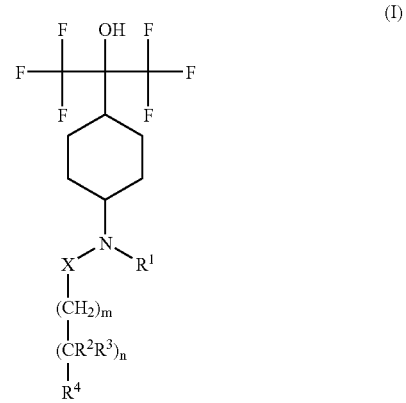

wherein $R^1$ to $R^4$, X, m and n are as defined in the description and in the claims, as well as physiologically acceptable salts and esters thereof. These compounds bind to LXR alpha and LXR beta and can be used as medicaments.

22 Claims, No Drawings

HEXAFLUOROISOPROPANOL SUBSTITUTED CYCLOHEXANE DERIVATIVES

PRIORITY TO RELATED APPLICATIONS

This application claims the benefit of priority to European Application No. 04106896.6, filed Dec. 22, 2004, which is hereby incorporated by reference in its entirety.

FIELD OF THE INVENTION

The invention is directed to novel hexafluoroisopropanol substituted cyclohexane derivatives of the formula (I)

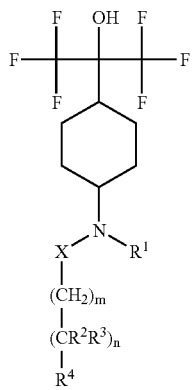

and pharmaceutically acceptable salts and esters thereof.

All documents cited or relied upon below are expressly incorporated herein by reference.

BACKGROUND OF THE INVENTION

Liver-X-Receptors (LXRs) are members of the nuclear hormone receptor superfamily. The LXRs are activated by endogenous oxysterols and regulate the transcription of genes controlling multiple metabolic pathways. Two sub-types, LXRalpha and LXRbeta, have been described (Willy et al., Genes Dev. 1995, 9:1033-45; Song et al., Proc Natl Acad Sci USA. 1994, 91:10809-13). LXRbeta is ubiquitously expressed, while LXRalpha is predominantly expressed in cholesterol metabolizing tissues such as the liver, adipose, intestine and macrophage. The LXRs modulate a variety of physiological responses including regulation of cholesterol absorption, cholesterol elimination (bile acid synthesis), and transport of cholesterol from peripheral tissues via plasma lipoproteins to the liver. The LXRs are also involved in glucose metabolism, cholesterol metabolism in the brain, cell differentiation, and inflammation.

At present, approximately half of all patients with coronary artery disease have low concentrations of plasma high-density lipoprotein cholesterol (HDL-C). The atheroprotective function of HDL was first highlighted almost 25 years ago and stimulated exploration of the genetic and environmental factors that influence HDL-C levels (Miller N E., Lipids 1978,13:914-9). The protective function of HDL derives from its role in a process termed reverse cholesterol transport. HDL mediates the removal of cholesterol from cells in peripheral tissues, including macrophage foam cells in the atherosclerotic lesions of the arterial wall. HDL delivers its cholesterol to the liver and sterol-metabolizing organs for conversion to bile and elimination in feces. Studies have shown that HDL-C levels are predictive of coronary artery disease risk independently of low-density lipoprotein cholesterol (LDL-C) levels (Gordon et al., Am J Med. 1977, 62:707-14).

At present, the estimated age-adjusted prevalence among Americans age 20 and older having HDL-C of less than 35 mg/dl is 16% (males) and 5.7% (females). A substantial increase of HDL-C is currently achieved by treatment with niacin in various formulations. However, the substantial unfavorable side-effects limit the therapeutic potential of this approach.

It has been observed that as many as 90% of the 14 million diagnosed type 2 diabetic patients in the United States are overweight or obese, and a high proportion of type 2 diabetic patients have abnormal concentrations of lipoproteins. Studies have shown that the prevalence of total cholesterol >240 mg/dl is 37% in diabetic men and 44% in women. The rates for LDL-C >160 mg/dl are 31% and 44%, and for HDL-C <35 mg/dl are 28% and 11%, in diabetic men and women respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and has been shown to afflict 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in the later stages of the disease, due to exhaustion and failure of pancreatic insulin-producing capacity. Thus, T2D is a cardiovascular-metabolic syndrome associated with multiple co-morbidities, including insulin resistance, dyslipidemia, hypertension, endothelial dysfunction and inflammatory atherosclerosis.

The first line of treatment for dyslipidemia and diabetes at present generally involves a low-fat and low-glucose diet, exercise and weight loss. However, compliance can be moderate, and as the disease progresses, treatment of the various metabolic deficiencies becomes necessary with lipid-modulating agents such as statins and fibrates for dyslipidemia, and hypoglycemic drugs, e.g. sulfonylureas, metformin, or insulin sensitizers of the thiazolidinedione (TZD) class of PPARγ-agonists, for insulin resistance.

Recent studies provide evidence that modulators of LXRs would result in compounds with enhanced therapeutic potential, and as such, modulators of LXRs should improve the plasma lipid profile, and raise HDL-C levels (Lund et al., Arterioscler. Thromb. Vasc. Biol. 2003, 23:1169-77). LXRs are also known to control the efflux of cholesterol from the macrophage foam cell of the atherosclerotic lesion, and agonists of LXRs have been shown to be atheroprotective (Joseph and Tontonoz, Curr. Opin. Pharmacol. 2003, 3:192-7). Thus, modulators of LXRs would be effective treatments for the atherosclerotic disease which underlies the cardiovascular morbidity and mortality of stroke and heart disease. Recent observations also suggest that there is an independent LXR mediated effect on insulin-sensitization in addition to its role in atheroprotection (Cao et al., J Biol. Chem. 2003, 278:1131-6). Thus LXR modulators can also show-superior therapeutic efficacy on HDL-raising and atheroprotection, with additional effects on diabetes, compared to current therapies.

Other compounds that bind to and activate LXR alpha and LXR beta have previously been suggested (e.g.: WO 03/099769). However, there is still a need in the art for new compounds with improved properties.

SUMMARY OF THE INVENTION

In one embodiment of the present invention, provided is a compound of formula (I)

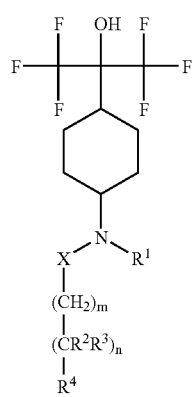

(I)

wherein

R¹ is hydrogen, lower-alkyl, fluoro-lower-alkyl, lower-alkyl-carbonyl, fluoro-lower-alkyl-carbonyl, aryl-lower-alkyl, cycloalkyl-lower-alkyl, cycloalkyl-carbonyl or cycloalkyl-lower-alkyl-carbonyl;

R² is hydrogen or lower-alkyl;

R³ is lower-alkyl, aryl-lower-alkyl, heterocyclyl-lower-alkyl or lower-alkoxy-carbonyl, or, if X is not a single bond, or, if X is a single bond and m is not 0, R³ can also be hydroxy;

R⁴ is aryl or heterocyclyl;

X is a single bond, $SO_2$, CO, C(O)O or $C(O)N(R^5)$;

R⁵ is hydrogen, lower-alkyl, aryl, heterocyclyl, aryl-lower-alkyl or heterocyclyl-lower-alkyl;

m is 0, 1, 2 or 3;

n is 0 or 1;

and pharmaceutically acceptable salts and esters thereof.

In another embodiment of the present invention, provided is a process for the manufacture of compounds of formula (I), comprising the steps of reacting a compound of formula (II)

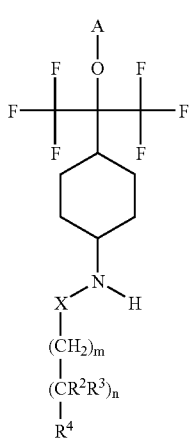

(II)

with a compound LG—R¹, wherein R¹, R², R³, R⁴, X, m and n are as defined above, A is hydrogen or a protecting group and LG is a leaving group, or reacting a compound of formula (III)

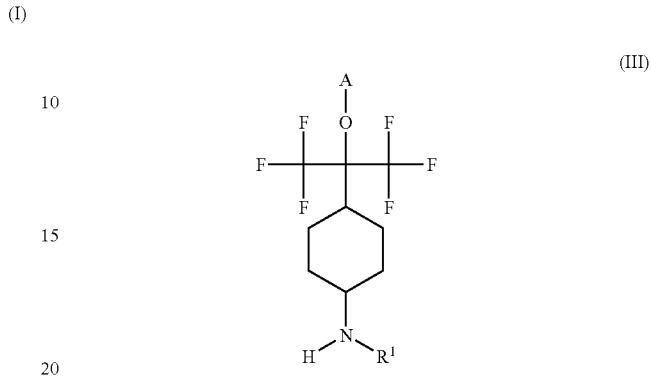

(III)

with a compound LG—X—$(CH_2)_m$—$(CR^2R^3)_n$—R⁴, wherein R¹, R², R³, R⁴, X, m and n are as defined above, A is hydrogen or a protecting group, LG is a leaving group, and removing the protecting group A.

In a further embodiment of the present invention, provided is a pharmaceutical composition, comprising a therapeutically defective amount of a compound according to formula (I) and a pharmaceutically acceptable carrier and/or adjuvant.

In a yet another embodiment of the present invention, provided is a method for the therapeutic and/or prophylactic treatment of diseases which are modulated by LXR alpha and/or LXR beta agonists, comprising the step of administering a therapeutically effective amount of a compound according to formula (I) to a human being or animal in need thereof.

DETAILED DESCRIPTION

The novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. Since multiple facets of combined dyslipidemia and cholesterol homeostasis are addressed by LXR modulators, novel compounds of the present invention have an enhanced therapeutic potential compared to the compounds already known in the art. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment and prophylaxis of age-related and inherited (e.g. Stargardt's disease) forms of macular degeneration.

The present invention provides the novel compounds of formula (I) which bind to LXR alpha and/or LXR beta. The compounds of the present invention exhibit improved pharmacological properties compared to the compounds known in the art, concerning e.g. metabolic stability, bioavailability and activity.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H—CF_2$.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl.

Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2$ CH—O, and $CF_2H$—$CF_2$—O.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups.

The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl", alone or in combination, relates to the phenyl or naphthyl group, preferably the phenyl group, which can optionally be substituted by 1 to 5, preferably 1 to 3, substituents independently selected from the group consisting of lower-alkyl, lower-alkoxy, halogen, hydroxy, CN, $CF_3$, amino, aminocarbonyl, carboxy, $NO_2$, dioxo-lower-alkylene (forming e.g. a benzodioxyl group), lower-alkylsufonyl, aminosulfonyl, lower-alkylcarbonyl, lower-alkylcarbonyloxy, lower-alkylcarbonyl-NH, lower-alkoxycarbonyl, fluoro-lower-alkyl, fluoro-lower-alkoxy, cycloalkyl and phenyloxy. Preferred substituents are halogen, lower-alkyl, fluoro-lower-alkyl, CN and lower-alkoxycarbonyl.

The term "heterocyclyl", alone or in combination, signifies a saturated, partially unsaturated or aromatic 5- to 10-membered, mono- or bicyclic heterocycle which contains one or more hetero atoms, preferably one to three, selected from nitrogen, oxygen and sulphur. If desired, it can be substituted on one or more carbon atoms e.g. by halogen, lower-alkyl, lower-alkoxy, oxo etc. and/or on a secondary nitrogen atom (i.e. —NH—) by lower-alkyl, cycloalkyl, phenyl-lower-alkoxycarbonyl, lower-alkylcarbonyl, phenyl or phenyl-lower-alkyl or on a tertiary nitrogen atom (i.e. =N—) by oxido, with halogen and lower-alkyl being preferred. Examples of such heterocyclyl groups are pyrrolidinyl, pyrrolyl, piperidinyl, piperazinyl, morpholinyl, thiomorpholinyl, pyrazoyl, triazolyl, tetrazolyl, isothiazolyl, imidazolyl (e.g. imidazol-4-yl and 1-benzyloxycarbonyl-imidazol-4-yl), benzoimidazolyl, pyrazolyl, pyridinyl, pyrazinyl, pyridazinyl, pyrimidinyl, hexahydro-pyrimidinyl, furyl, thienyl, thiazolyl, oxazolyl, isoxazolyl, indolyl (e.g. 2-indolyl), indazolyl, quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl), tetrahydropyranyl, quinoxalinyl, oxopyrrolidinyl and benzo[b]thiophenyl. Preferred are thiazolyl, imidazolyl and pyrazolyl. A heterocyclyl group may also have a substitution pattern as described earlier in connection with the term "aryl". Aromatic heterocyclyl groups are preferred.

The term "leaving group" refers to a group that may be displaced by a nucleophile (e.g. a secondary amine). Typical leaving groups are e.g.: Cl, Br, I, O—$SO_2$-lower-alkyl (wherein O—$SO_2$—$CH_3$=OMs), O—$SO_2$-fluoro-lower-alkyl (wherein O—$SO_2$—$CF_3$=OTf), O—$SO_2$-aryl (wherein O—$SO_2$-ptolyl=OTs), O-(para-nitrophenyl).

The term "protecting group" refers to groups which are used to protect functional groups, particularly hydroxy groups, temporarily. Examples of protecting groups are benzyl, p-methoxybenzyl, t-butyl-dimethylsilyl, triethylsilyl, triisopropylsilyl and t-butyl-diphenylsilyl.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts. Salts obtained by the addition of a base are preferred.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

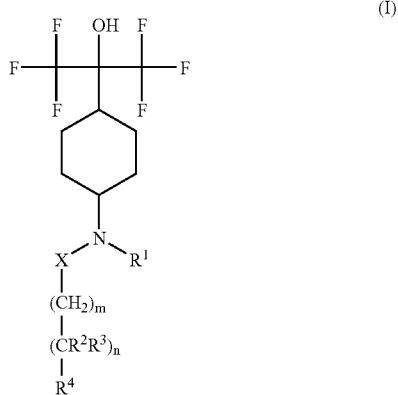

(I)

wherein $R^1$ is hydrogen, lower-alkyl, fluoro-lower-alkyl, lower-alkyl-carbonyl, fluoro-lower-alkyl-carbonyl, aryl-lower-alkyl, cycloalkyl-lower-alkyl, cycloalkyl-carbonyl or cycloalkyl-lower-alkyl-carbonyl;

$R^2$ is hydrogen or lower-alkyl;

$R^3$ is lower-alkyl, aryl-lower-alkyl, heterocyclyl-lower-alkyl or lower-alkoxy-carbonyl, or, if X is not a single bond, or, if X is a single bond and m is not 0, $R^3$ can also be hydroxy;

$R^4$ is aryl or heterocyclyl;

X is a single bond, $SO_2$, CO, C(O)O or $C(O)N(R^5)$;

$R^5$ is hydrogen, lower-alkyl, aryl, heterocyclyl, aryl-lower-alkyl or heterocyclyl-lower-alkyl;

m is 0, 1, 2 or 3;

n is 0 or 1;

and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) have two or more asymmetric C atoms and can therefore exist as an enantiomeric mixture, mixture of stereoisomers or as optically pure compounds.

Preferred compounds of the present invention are the trans-compounds. Preferred compounds of formula (I) as described above are those characterised by formula (IA)

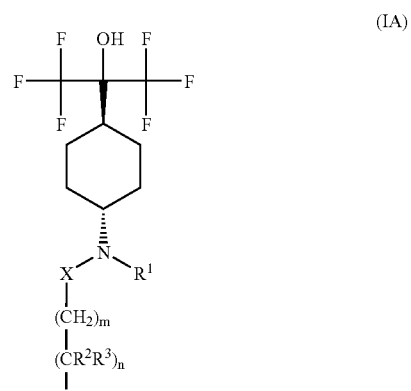

(IA)

wherein $R^1$, $R^2$, $R^3$, $R^4$, X, m and n are as defined above, and pharmaceutically acceptable salts and esters thereof.

Preferred compounds of formula (I) as described above are those, wherein $R^1$ is hydrogen, lower-alkyl, fluoro-lower-alkyl, lower-alkyl-carbonyl, fluoro-lower-alkyl-carbonyl, aryl-lower-alkyl, cycloalkyl-lower-alkyl or cycloalkyl-carbonyl. Preferably, $R^1$ is fluoro-lower-alkyl, aryl-lower-alkyl or cycloalkyl-lower-alkyl. More preferably, $R^1$ is 2,2,2-trifluoroethyl, benzyl or cyclopropylmethyl.

Other preferred compounds of formula (I) as described above are those, wherein n is 1, $R^2$ is hydrogen or lower-alkyl, and $R^3$ is lower-alkyl, aryl-lower-alkyl or lower-alkoxy-carbonyl, or, if X is not a single bond, or, if X is a single bond and m is not 0, $R^3$ can also be hydroxy. Preferably, $R^2$ is lower-alkyl. More preferably, $R^2$ is methyl. Other preferred compounds are those, wherein $R^3$ is lower-alkyl, particularly wherein $R^3$ is methyl.

Another preferred embodiment of the present invention relates to compounds of formula (I) as described above, wherein $R^4$ is aryl or a heterocyclyl selected from the group consisting of thiazolyl, imidazolyl and pyrazolyl, which thiazolyl, imidazolyl or pyrazolyl is optionally substituted with 1 to 3 substituents independently selected from the group of lower-alkyl and halogen. Compounds wherein $R^4$ is aryl are particularly preferred, especially those, wherein $R^4$ is phenyl.

Other preferred compounds of formula (I) as described above are those, wherein m is 0 or 1. Compounds wherein m is 0 and compounds wherein m is 1 individually constitute preferred embodiments of the present invention. Preferably, m is 0. Another preferred embodiment of the present invention relates to compounds as defined above, wherein n is 0.

Another preferred embodiment of the present invention relates to compounds of formula (I) as described above, wherein X is a single bond, $SO_2$, CO or C(O)O. Preferably, X is $SO_2$.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of:

trans N-(2,2,2-Trifluoro-ethyl)-N-[4-(2,2,2-trifluoro-1-hydroxy-1-trifluoromethyl-ethyl)-cyclohexyl]-benzenesulfonamide, trans N-[4-(2,2,2-Trifluoro-1-hydroxy-1-trifluoromethyl-ethyl)-cyclohexyl]-benzenesulfonamide, trans N-Benzyl-2,2,2-trifluoro-N-[4-(2,2,2-trifluoro-1-hydroxy-1-trifluoromethyl-ethyl)-cyclohexyl]-acetamide, trans Phenyl-[4-(2,2,2-trifluoro-1-hydroxy-1-trifluoromethyl-ethyl)-cyclohexylamino]-acetic acid ethyl ester, trans N-Benzyl-N-[4-(2,2,2-trifluoro-1-hydroxy-1-trifluoromethyl-ethyl)-cyclohexyl]-acetamide, trans N-Benzyl-N-[4-(2,2,2-trifluoro-1-hydroxy-1-trifluoromethyl-ethyl)-cyclohexyl]-benzenesulfonamide, trans 2,4-Dimethyl-thiazole-5-sulfonic acid [4-(2,2,2-trifluoro-1-hydroxy-1-trifluoromethyl-ethyl)-cyclohexyl]-amide, trans 1,2-Dimethyl-1H-imidazole-4-sulfonic acid [4-(2,2,2-trifluoro-1-hydroxy-1-trifluoromethyl-ethyl)-cyclohexyl]-amide, trans 1,2-Dimethyl-1H-imidazole-4-sulfonic acid (2,2,2-trifluoro-ethyl)-[4-(2,2,2-trifluoro-1-hydroxy-1-trifluoromethyl-ethyl)-cyclohexyl]-amide, trans 1,2-Dimethyl-1H-imidazole-4-sulfonic acid ethyl-[4-(2,2,2-trifluoro-1-hydroxy-1-trifluoromethyl-ethyl)-cyclohexyl]-amide, trans 4-Methyl-2-propyl-thiazole-5-sulfonic acid ethyl-[4-(2,2,2-trifluoro-1-hydroxy-1-trifluoromethyl-ethyl)-cyclohexyl]-amide, trans 2,4-Dimethyl-thiazole-5-sulfonic acid (2,2,2-trifluoro-ethyl)-[4-(2,2,2-trifluoro-1-hydroxy-1-trifluoromethyl-ethyl)-cyclohexyl]-amide, trans 2,4-Dimethyl-thiazole-5-sulfonic acid cyclopropylmethyl-[4-(2,2,2-trifluoro-1-hydroxy-1-trifluoromethyl-ethyl)-cyclohexyl]-amide, trans 2,4-Dimethyl-thiazole-5-sulfonic acid ethyl-[4-(2,2,2-trifluoro-1-hydroxy-1-trifluoromethyl-ethyl)-cyclohexyl]-amide, trans N-Cyclopropylmethyl-N-[4-(2,2,2-trifluoro-1-hydroxy-1-trifluoromethyl-ethyl)-cyclohexyl]-benzenesulfonamide, trans N-Ethyl-N-[4-(2,2,2-trifluoro-1-hydroxy-1-trifluoromethyl-ethyl)-cyclohexyl]-benzenesulfonamide, trans 5-Chloro-1,4-dimethyl-1H-pyrazole-3-sulfonic acid (2,2,2-trifluoro-ethyl)-[4-(2,2,2-trifluoro-1-hydroxy-1-trifluoromethyl-ethyl)-cyclohexyl]-amide, trans 5-Chloro-1,4-dimethyl-1H-pyrazole-3-sulfonic acid [4-(2,2,2-trifluoro-1-hydroxy-1-trifluoromethyl-ethyl)-cyclohexyl]-amide, trans 2-[4-(Benzyl-ethyl-amino)-cyclohexyl]-1,1,1,3,3,3-hexafluoro-propan-2-ol, trans 2-[4-(Benzyl-propyl-amino)-cyclohexyl]-1,1,1,3,3,3-hexafluoro-propan-2-ol, trans 2-[4-(Benzyl-cyclopropylmethyl-amino)-cyclohexyl]-1,1,1,3,3,3-hexafluoro-propan-2-ol, trans N-Benzyl-N-[4-(2,2,2-trifluoro-1-hydroxy-1-trifluoromethyl-ethyl)-cyclohexyl]-propionamide, trans Cyclopropanecarboxylic acid benzyl-[4-(2,2,2-trifluoro-1-hydroxy-1-trifluoromethyl-ethyl)-cyclohexyl]-amide, trans N-Cyclopropylmethyl-N-[4-(2,2,2-trifluoro-1-hydroxy-1-trifluoromethyl-ethyl)-cyclohexyl]-benzamide, trans N-Cyclopropylmethyl-2-phenyl-N-[4-(2,2,2-trifluoro-1-hydroxy-1-trifluoromethyl-ethyl)-cyclohexyl]-acetamide, trans Cyclopropylmethyl-[4-(2,2,2-trifluoro-1-hydroxy-1-trifluoromethyl-ethyl)-cyclohexyl]-carbamic acid phenyl ester, trans Cyclopropylmethyl-[4-(2,2,2-trifluoro-1-hydroxy-1-trifluoromethyl-ethyl)-cyclohexyl]-carbamic acid benzyl ester, (rac) trans 2-{4-[cyclopropylmethyl-(2-hydroxy-2-phenyl-ethyl)-amino]-cyclohexyl}-1,1,1,3,3,3-hexafluoro-propan-2-ol, trans Benzyl-N-[4-(2,2,2-trifluoro-1-hydroxy-1-trifluoromethyl-ethyl)-cyclohexyl]-sulfonamide, trans Benzyl-N-(2,2,2-trifluoro-ethyl)-N-[4-(2,2,2-trifluoro-1-hydroxy-1-trifluoromethyl-ethyl)-cyclohexyl]-sulfonamide, (rac) trans 1-Phenyl-ethanesulfonic acid (2,2,2-trifluoro-ethyl)-[4-(2,2,2-trifluoro-1-hydroxy-1-trifluoromethyl-ethyl)-cyclohexyl]-amide, trans 2-Phenyl-propane-2-sulfonic acid (2,2,2-trifluoro-ethyl)-[4-(2,2,2-trifluoro-1-hydroxy-1-trifluoromethyl-ethyl)-cyclohexyl]-amide, (rac) trans 1,2-diphenyl-ethanesulfonic acid (2,2,2-trifluoro-ethyl)-[4-(2,2,2-trifluoro-1-hydroxy-1-trifluoromethyl-ethyl)-cyclohexyl]-amide, (rac) trans 3-(2-Phenyl-2-{(2,2,2-trifluoro-ethyl)-[4-(2,2,2-trifluoro-1-hydroxy-1-trifluoromethyl-ethyl)-cyclohexyl]-sulfamoyl}-ethyl)-benzoic acid methyl ester, and cis N-Ethyl-N-[4-(2,2,2-trifluoro-1-hydroxy-1-trifluoromethyl-ethyl)-cyclohexyl]-benzenesulfonamide, and pharmaceutically acceptable salts and esters thereof.

Particularly preferred compounds of formula (I) are those selected from the group consisting of:

trans N-(2,2,2-Trifluoro-ethyl)-N-[4-(2,2,2-trifluoro-1-hydroxy-1-trifluoromethyl-ethyl)-cyclohexyl]-benzenesulfonamide, trans N-Benzyl-N-[4-(2,2,2-trifluoro-1-hydroxy-1-trifluoromethyl-ethyl)-cyclohexyl]-benzenesulfonamide, trans N-Cyclopropylmethyl-N-[4-(2,2,2-trifluoro-1-hydroxy-1-trifluoromethyl-ethyl)-cyclohexyl]-benzenesulfonamide, trans Benzyl-N-(2,2,2-trifluoro-ethyl)-N-[4-(2,2,2-trifluoro-1-hydroxy-1-trifluoromethyl-ethyl)-cyclohexyl]-sulfonamide, and trans 2-Phenyl-propane-2-sulfonic acid (2,2,2-trifluoro-ethyl)-[4-(2,2,2-trifluoro-1-hydroxy-1-trifluoromethyl-ethyl)-cyclohexyl]-amide, and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (II)

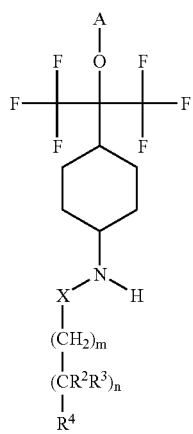

with a compound LG—R¹,
wherein $R^1$, $R^2$, $R^3$, $R^4$, X, m and n are as defined above, A is hydrogen or a protecting group and LG is a leaving group (such as e.g. I, Br, Cl, triflate, mesylate, tosylate),
or
reacting a compound of formula (III)

with a compound LG—X—$(CH_2)_m$—$(CR^2R^3)_n$—$R^4$, wherein $R^1$, $R^2$, $R^3$, $R^4$, X, m and n are as defined above, A is hydrogen or a protecting group, LG is a leaving group (such as e.g. I, Br, Cl, or, if X is a single bond, LG can also be e.g. triflate, mesylate, tosylate), and removing the protecting group A.

The reaction of a compound of formula (II) with a compound LG—R¹ and removing of the protecting group A if necessary can be carried out under conditions well known to the person skilled in the art. Such reactions of a compound of formula (II) can conveniently be carried out after treatment with a strong base such as e.g. lithium bis(trimethylsilyl) amide or in some cases in the presence of a base such as e.g. DBU in a solvent such as e.g. THF or DMF at a suitable temperature. The reaction of a compound of formula (III) with a compound LG—X—$(CH_2)_m$—$(CR^2R^3)_n$—$R^4$, and removing of the protecting group A if necessary can be carried out under conditions well known to the person skilled in the art. Such reactions of a compound of formula (III) can conveniently be carried out in the presence of a base such as e.g. $NEt_3$ in a solvent such as e.g. dichloromethtane or THF at a suitable temperature. The protecting group is removed using standard deprotection methods commonly known in the art, such as e.g. desilylation using TBAF.

The present invention also relates to compounds of formula (I) as defined above, when prepared by a process as described above.

The compounds of formula (I) can be prepared by methods known in the art or as described below. Unless otherwise indicated, the substituents $R^1$, $R^2$, $R^3$, $R^4$, $R^5$, X, m and n are as described above.

Preparation of derivatives in which $R^1$ is hydrogen is carried out as described below in scheme 1.

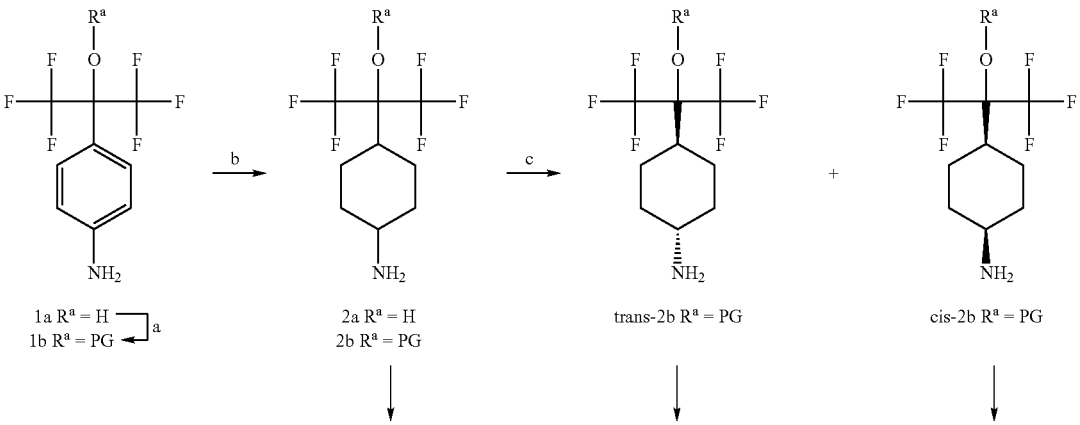

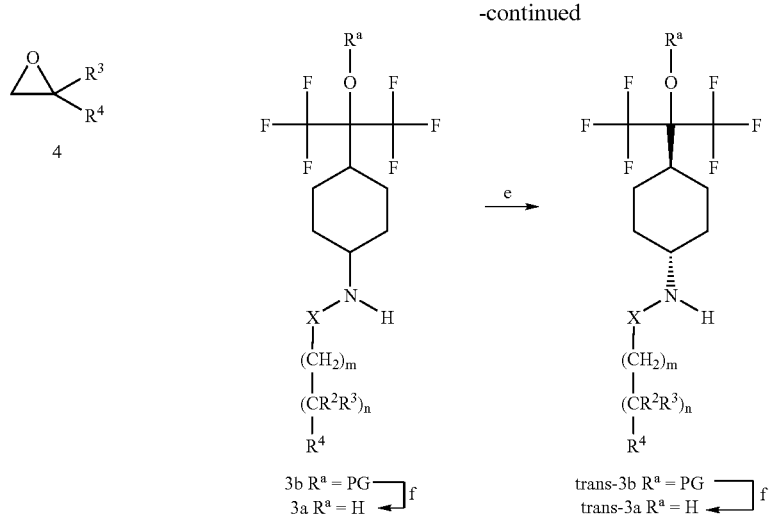
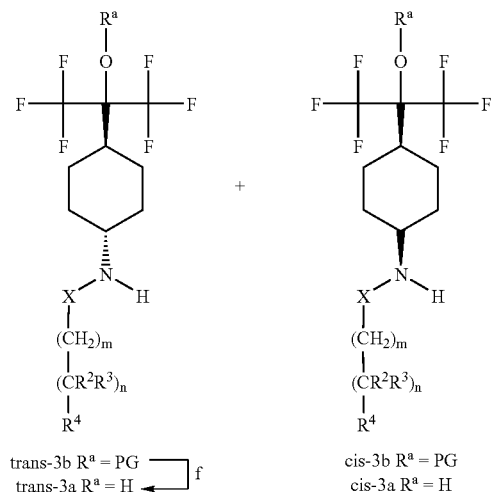

Aniline 1a may be O-protected to 1b (step a) with a suitable protecting group "PG" such as e.g. a triethylsilyl or a t-butyldimethylsilyl group by treatment with a silylating agent (e.g. triethylsilylchloride or t-butyldimethylsilyl chloride, respectively) in the presence of a suitable base (e.g. DBU, imidazole). Unprotected aniline 1a or protected aniline 1b may be converted to a ca. 1:1-trans/cis-mixture of cyclohexanes 2a and 2b, respectively, by hydrogenation in a suitable solvent such as AcOH, methanol or ethanol in the presence of a catalyst such as e.g. Pt on charcoal or $PtO_2$ under acidic conditions (step b). Filtration and evaporation of the solvent leads to 2a or 2b in the form of their ammonium salts with the deprotonated acid as counter anion. The free amines can be obtained by basic work up (e.g. distribution between an aqueous NaOH-solution and AcOEt). The free amines of the trans and cis isomers trans-2b and cis-2b may be separated by chromatography (step c).

The introduction of the "$X-(CH_2)_m-(CR^2R^3)_n-R^4$"-moiety (step d) leading to derivatives 3a, 3b or trans-3b or cis-3b can be carried out by one of the methods described below. To obtain compounds 3a, 3b, trans-3b or cis-3b in which X=single bond, 2a, 2b, trans-2b or cis-2b may be treated with an aldehyde $CHO-(CH_2)_{m-1}-(CR^2R^3)_n-R^4$ (wherein m=1-3) in presence of a reducing agent such as e.g. $NaBCNH_3$ in a suitable solvent such as e.g. ethanol or methanol. The use of a ketone $R^3-CO-R^4$ instead of $CHO-(CH^2)_{m-1}-(CR^2R^3)_n-R^4$ leads to derivatives with X=single bond, m=0, n=1 and $R^2$=H. Alternatively 2a, but preferably 2b, trans-2b, or cis-2b may be treated with an alkylating agent $LG-(CH_2)_m-(CR^2R^3)_n-R^4$, wherein LG is a leaving group such as e.g. Cl, Br, I, $OSO_2$aryl, $OSO_2CH_3$, $OSO_2CF_3$. Such alkylations are preferably carried out in presence of a base (e.g. $K_2CO_3$) in a suitable solvent such as e.g. acetonitrile, DMF, DMA or THF. To obtain compounds 3a, 3b, trans-3b or cis-3b in which X=CO, COO, $CONR^5$, or $SO_2$, 2a, 2b, trans-2b or cis-2b may be treated with a chloride $Cl-X-(CH_2)_m-(CR^2R^3)_n-R^4$ in the presence of a suitable base such as e.g. DIPEA, $NEt_3$ or N-methylmorpholine. For X=CO and $SO_2$, 3a, 3b, trans-3b or cis-3b may also be obtained by treatment with a carboxylic acid $HOCO-(CH_2)_m-(CR^2R^3)_n-R^4$ or a sulfonic acid $HOSO_2-(CH_2)_m-(CR^2R^3)_n-R^4$ in the presence of a typical peptide coupling reagent such as e.g. EDCI or DCC (if required in combination with 1-hydroxybenzotriazole) in a suitable solvent (e.g. dichloromethane, THF or DMF). Compounds 3a, 3b trans-3b or cis-3b in which X=CONH may also be obtained by treatment of 2a, 2b, trans-2b or cis-2b with an isocyanate $O=C=N-(CH_2)_m-(CR^2R^3)_n-R^4$. Derivatives in which $R^3$=hydroxy, X=single bond, and m=1, can be prepared by treatment of 2a, 2b, trans-2b or cis-2b with an oxirane 4.

Trans-3a, trans-3b and the corresponding cis analogues can be obtained whenever desired or required from 3a and 3b, respectively, by chromatography (step e). Removal of the protecting group (step f) is carried out according to commonly known standard procedures such as described e.g. in "Protective groups in organic chemistry" by T. W. Greene and P. G. M. Wutts, $2^{nd}$ Ed., 1991, N.Y. (e.g. desilylation using tetrabutylammonium fluoride).

Preparation of derivatives in which $R^1$ is lower alkyl, fluoro-lower-alkyl, lower-alkyl-carbonyl, fluoro-lower-alkyl-carbonyl, aryl-lower-alkyl, cycloalkyl-lower-alkyl, cycloalkyl-carbonyl, cycloalkyl-lower-alkyl-carbonyl is carried out by one of the methods described below in scheme 2.

Scheme 2

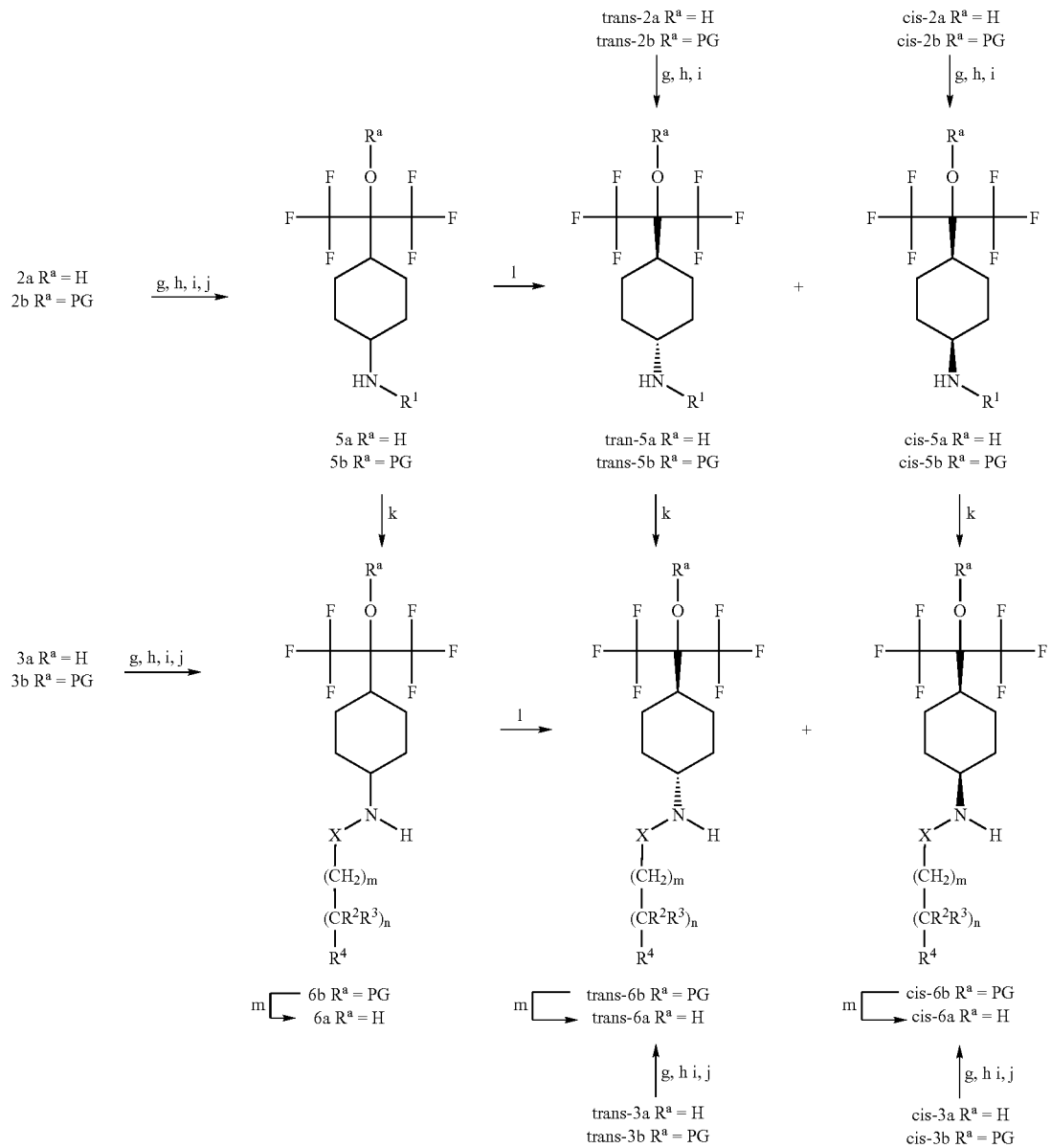

Treatment of 2a, 2b, trans-2a) trans-2b, cis-2a or cis-2b with an acylating agent such as e.g. an acylchloride $R^1$—Cl or an acid anhydride $(R^1)_2O$, wherein $R^1$=lower-alkyl-carbonyl, fluoro-lower-alkyl-carbonyl, cycloalkyl-carbonyl, cycloalkyl-lower-alkyl-carbonyl in the presence of a base such as DIPEA, $NEt_3$ or N-methylmorpholine in a solvent such as e.g. dichloromethane, THF or DMF leads to derivatives 5a, 5b, trans-5a, trans-5b cis-5a or cis-5b (step g). Alternatively these acylations may be carried out with the carboxylic acid in the presence of a typical peptide coupling reagent such as e.g. EDCI or DCC (if required in combination with 1-hydroxybenzotriazole) in a suitable solvent (e.g. dichloromethane, THF or DMF).

Optionally the carbonyl group can be subsequently removed by treatment with a reducing agent such as e.g. $BH_3$ in a solvent such as THF leading to derivatives 5a, 5b, trans-5a, trans-5b, cis-5a or cis-5b with $R^1$=lower alkyl, fluoro-lower-alkyl, cycloalkyl-lower-alkyl (step h). These latter derivatives may also be obtained by treatment of 2a, 2b, trans-2a, trans-2b cis-2a or cis-2b with a suitable aldehyde or ketone in the presence of a reducing agent such as e.g. $NaBCNH_3$ (step i) or by treatment with an alkylating agent such as lower-alkyl-LG, fluoro-lower-alkyl-LG, aryl-lower-alkyl-LG, cycloalkyl-lower-alkyl-LG, wherein LG is a leaving group such as e.g. Cl, Br, I, $OSO_2$aryl, $OSO_2CH_3$, $OSO_2CF_3$ (step j). The treatment with the alkylating agent is carried out preferably in presence of a base (e.g. DBU, $K_2CO_3$) or after deprotonation of 2a, 2b, trans-2a, trans-2b, cis-2a, cis-2b, with a strong base (e.g. lithium bis (trimethylsilyl)amide or lithium diisopropylamide). The same methods g-j can be used to convert 3a, 3b, trans-3a, trans-3b, cis-3a, cis-3b, into 6a, 6b, trans-6a, trans-6b, cis-6a, cis-6b, respectively. For derivatives 5a, 5b, trans-5a, trans-5b, cis-5a or cis-5b in which $R^1$ is restricted to $R^1$=lower alkyl, fluoro-lower-alkyl, aryl-lower-alkyl, cycloalkyl-lower-alkyl, the "X—(CH$_2$)$_m$—(CR$^2$R$^3$)$_n$—R$^4$-moiety can be introduced by one of the methods described in step d of scheme 1 (step k).

Deprotonation of derivatives 6b, trans-6b or cis-6b with X=SO$_2$, CO, m=1 and n=0 with a strong base (e.g. lithium bis (trimethylsilyl)amide or lithium diisopropylamide) and subsequent treatment with O$_2$, lower-alkyl-LG, aryl-lower-alkyl-LG, heterocyclyl-lower-alkyl-LG (wherein LG is a leaving group such as e.g. Cl, Br, I, OSO$_2$aryl, OSO$_2$CH$_3$, OSO$_2$CF$_3$) leads to derivatives 6b, trans-6b or cis-6b with R$^3$=hydroxy, lower-alkyl, aryl-lower-alkyl, heterocyclyl-lower-alkyl, respectively, and X=SO$_2$, CO, m=0, and n=1.

Derivatives 6 or trans-6b or cis-6b with X=SO$_2$, CO, m=0 and n=1 may also be deprotonated with a strong base such as e.g. lithium bis (trimethylsilyl)amide or lithium diisopropylamide and subsequently be treated with a alkylating agent "lower alkyl-LG" (wherein LG is a leaving group such as e.g. Cl, Br, I, OSO$_2$aryl, OSO$_2$CH$_3$, OSO$_2$CF$_3$) to give derivatives 6, trans-6b or cis-6b with X=SO$_2$, CO, m=0, n=1 and R$^2$=lower alkyl.

Trans-5a, trans-5b, trans-6a, trans-6b and the corresponding cis analogues can be obtained whenever desired or required from 3a and 3b, respectively, by chromatography (step l). Removal of the protecting group (step m) is carried out according to commonly known standard procedures such as described e.g. in "Protective groups in organic chemistry" by T. W. Greene and P. G. M. Wutts, 2$^{nd}$ Ed., 1991, N.Y. (e.g. desilylation using tetrabutylammonium fluoride).

A large number of the compounds Cl—X—(CH$_2$)$_m$—(CR$^2$R$^3$)$_n$—R$^4$, CHO—(CH$_2$)$_{m-1}$—(CR$^2$R$^3$)$_n$—R$^{4'}$, LG—(CH$^2$)$_m$—(CR$^2$R$^3$)$_n$—R$^4$ are commercially available. If not, they may be prepared from a related commercially available starting material such as e.g. an ester alkylOCO—(CH$_2$)$_{m-1}$—(CR$^2$R$^3$)$_n$—R$^4$, a carboxylic acid HOCO—(CH$_2$)$_{m-1}$—(CR$^2$R$^3$)$_n$—R$^4$, an alcohol HO—(CH$_2$)$_m$—(CR$^2$R$^3$)$_n$—R$^4$ or for X=SO$_2$ e.g. a sulfonic acid HOSO$_2$—(CH$_2$)$_m$—(CR$^2$R$^3$)$_n$—R$^4$ according to standard literature procedures commonly known to those of the art. A selection of three typical examples for such transformations are e.g.: 1) the transformation of a carboxylic acid HOCO—(CH$_2$)$_{m-1}$—(CR$^2$R$^3$)$_n$—R$^4$ into the corresponding carboxylic acid chloride Cl—CO—(CH$^2$)$_{m-1}$—(CR$^2$R$^3$)$_n$—R$^4$ by treatment with e.g. SOCl$_2$ or POCl$_3$ in a suitable solvent such as e.g. dichloromethane; 2) the oxidation of an alcohol HO—(CH$_2$)$_m$—(CR$^2$R$^3$)$_n$—R$^4$n into an aldehyde CHO—(CH$^2$)$_{m-1}$—(CR$^2$R$^3$)$_n$—R$^4$ (e.g. by a Swern-oxidation); 3) the transformation of an alcohol HO—(CH$_2$)$_m$—(CR$^2$R$^3$)$_n$—R$^4$ into a derivative LG—(CH$_2$)$_m$—(CR$^2$R$^3$)$_n$—R$^4$ using e.g. PBr$_3$ to obtain the derivative with LG=Br, or using e.g. methanesulfonylchloride (in the presence of a base such as e.g. NEt$_3$) to obtain the derivative with LG=OSO$_2$CH$_3$.

Epoxides 4—if not commercially available—may be obtained by epoxidation of an alkene CH$_2$=CR$^3$R$^4$ with a commonly used epoxidizing agent such as e.g. meta chloro perbenzoic acid in a suitable solvent such as e.g. dichloromethane.

If 3a, 3b, 6a, 6b, trans-3a, trans-3b, trans-6a, trans-6b, cis-3a, cis-3b, cis-6a or cis-6b contain a functional group not compatible with one of the transformations described above, this functional group may be suitably protected prior to the transformation(s) and deprotected again at a later stage. Such protections and deprotections are carried out according to standard literature procedures as described e.g. in "Protective groups in organic chemistry" by T. W. Greene and P. G. M. Wutts, 2$^{nd}$ Ed., 1991, N.Y." and are commonly known to those of the art.

The conversion of a compound of formula (I) into a pharmaceutically acceptable salt can be carried out by treatment of such a compound with an inorganic acid, for example a hydrohalic acid, such as, for example, hydrochloric acid or hydrobromic acid, or other inorganic acids such as sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. One method to form such a salt is e.g. by addition of 1/n equivalents of the acid, wherein n=number of acidic protons on the acid, to a solution of the compound in a suitable solvent (e.g. ethanol, ethanol-water mixture, tetrahydrofurane-water mixture) and to remove the solvent by evaporation or lyophilisation. Compounds of formula (I) can further form salts with physiologically compatible bases. Examples of such salts are alkaline, earth-alkaline and ammonium salts such as e.g. Na—, K—, Ca— and trimethylammoniumsalt. One method to form such a salt e.g. is by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofurane-water mixture) and to remove the solvent by evaporation or lyophilisation.

The conversion of compounds of formula (I) into pharmaceutically acceptable esters can be carried out e.g. by treatment of suitable amino or hydroxy groups present in the molecules with an carboxylic acid such as acetic acid, with a condensating reagent such as benzotriazol-1-yloxytris (dimethylamino)phosphonium hexafluorophosphate (BOP), N,N-dicylohexylcarbodiimide (DCC), N-(3-dimethylamino-propyl)-N'-ethylcarbodiimide hydrochloride (EDCI) or O-(1,2-dihydro-2-oxo-1-pyridyl)-N,N,N,N-tetra-methyluronium-tetrafluorborate (TPTU) to produce the carboxylic ester or carboxylic amide. Pharmaceutically acceptable esters can also be prepared by treatment of suitable carboxy groups present in the molecules with a suitable alcohol using e.g. one of the condensating agents mentioned above.

Insofar as their preparation is not described in the examples, the compounds of formula (I) as well as all intermediate products can be prepared according to analogous methods or according to the methods set forth above. Starting materials are commercially available or known in the art.

As described above, the novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment and prophylaxis of age-related and inherited (e.g. Stargardt's disease) forms of macular degeneration.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by LXR alpha and/or LXR beta agonists, particularly as therapeutically active substances for the treatment and/or prophylaxis of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease.

In another preferred embodiment, the invention relates to a method for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease, which method comprises administering a compound as defined above to a human being or animal.

The invention also embraces the use of compounds as defined above for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease.

The invention also relates to the use of compounds as described above for the preparation of medicaments for the therapeutic and/or prophylactic treatment of diseases which are modulated by LXR alpha and/or LXR beta agonists, particularly for the therapeutic and/or prophylactic treatment of increased lipid levels) increased cholesterol levels, low HDL-cholesterol, high LDL-cholesterol, atherosclerotic diseases, diabetes, non-insulin dependent diabetes mellitus) metabolic syndrome, dyslipidemia, sepsis, inflammatory diseases, skin diseases, colitis, pancreatitis, cholestasis of the liver, fibrosis of the liver, macular degeneration and/or Alzheimer's disease.

Such medicaments comprise a compound as described above.

Prevention and/or treatment of increased lipid levels, increased cholesterol levels, atherosclerotic diseases, dyslipidemia, or diabetes is the preferred indication, particularly prevention and/or treatment of increased lipid levels, increased cholesterol levels, atherosclerotic diseases, or dyslipidemia) especially prevention and/or treatment of atherosclerotic diseases or dyslipidemia. Diabetes, particularly non-insulin dependent diabetes mellitus, is another preferred disease.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following Examples serve to illustrate the present invention in more detail. They are, however, not intended to limit its scope in any manner.

EXAMPLES

Abbreviations:

AcOH=acetic acid, nBuLi=n-butyl lithium, $CH_2Cl_2$=dichloromethane, DBU=1,8-diazabicyclo[5.4.0]undec-7-ene, DIPEA=N-ethyldiisopropylamine, DMF=dimethylformamide, EtOAc=ethyl acetate, EtOH=ethanol, $Et_2O$=diethyl ether, heptane=n-heptane, i.v.=intra vacuum, MeOH=methanol, TBAF=tetrabutylammonium fluoride, TESCl=triethylchlorosilane, TFA=trifluoroacetic acid, THF=tetrahydrofurane, RT=room temperature.

General Remarks

All reactions were performed under argon.

Example 1 trans N-(2,2,2-trifluoro-ethyl)-N-[4-(2,2,2-trifluoro-1-hydroxy-1-trifluoromethyl-ethyl)-cyclohexyl]-benzenesulfonamide 1.1

A solution of 10 g (38.6 mmol) of 2-(4-amino-phenyl)-1,1,1,3,3,3-hexafluoro-propan-2-ol in 100 mL of DMF was treated with 6.3 mL (42.4 mmol) of DBU and then dropwise with 6.5 mL (38.6 mmol) of TESCl. After stirring the mixture at RT overnight the solvent was partially evaporated i.v. Distribution of the crude mixture between a diluted aqueous solution of NaOH and Et$_2$O and drying of the combined organic phases over Na$_2$SO$_4$ gave 13 g (90%) of 4-(2,2,2-trifluoro-1-triethylsilanyloxy-1-trifluoromethyl-ethyl)-phenylamine as a colorless oil, MS: 374 (M+H)$^+$.

1.2

A solution of 5 g (13.4 mmol) of 4-(2,2,2-trifluoro-1-triethylsilanyloxy-1-trifluoromethyl-ethyl)-phenylamine in 150 mL of AcOH was treated with 2.5 g of Pt/C (10%) and hydrogenated for 72 hrs at atmospheric pressure under intense stirring. Filtration and evaporation of the solvent gave a yellow semisolid that was distributed between a 1M aqueous solution of NaOH and EtOAc. The combined organic phases were dried over Na$_2$SO$_4$ and evaporated to yield 4 g of crude product. Chromatography on silica gel with EtOAc and then EtOAc/MeOH 10:1 gave ca. 1.9 g (37%) of cis-4-(2,2,2-trifluoro-1-triethylsilanyloxy-1-trifluoromethyl-ethyl)-cyclohexylamine and ca. 1.9 g (37%) trans-4-(2,2,2-trifluoro-1-triethylsilanyloxy-1-trifluoromethyl-ethyl)-cyclohexylamine as a light yellow oil, MS: 380 (M+H)$^+$.

1.3

A solution of 0.71 g (1.87 mmol) of trans 4-(2,2,2-trifluoro-1-triethylsilanyloxy-1-trifluoromethyl-ethyl)-cyclohexylamine in 5 mL of CH$_2$Cl$_2$ was treated with 0.64 mL (3.74 mmol) of DIPEA and 0.24 mL (1.87 mmol) of benzenesulfonylchloride and stirred at RT for 3 hrs. Distribution of the crude mixture between a diluted aqueous solution of HCl and Et$_2$O, drying of the combined organic phases over Na$_2$SO$_4$ and chromatography on silica gel with EtOAc/heptane 1:1 gave 0.9 g (93%) of trans-N-[4-(2,2,2-trifluoro-1-triethylsilanyloxy-1-trifluoromethyl-ethyl)-cyclohexyl]-benzenesulfonamide as a light yellow semisolid, MS: 518 (M-H).

1.4

A solution of 0.45 g (0.87 mmol) of trans N-[4-(2,2,2-trifluoro-1-triethylsilanyloxy-1-trifluoromethyl-ethyl)-cyclohexyl]-benzenesulfonamide in 5 mL of dry THF was cooled to −78° C. and treated dropwise with 0.7 mL (1.13 mmol) of a 1.6M solution of nBuLi in hexane. The solution was warmed to −40° C., treated with 1.0 g (4.33 mmol) of trifluoro-methanesulfonic acid 2,2,2-trifluoro-ethyl ester and then allowed to reach RT. The mixture was stirred for 30 min at RT and then refluxed for 2 hrs. The solvent was evaporated, the residue redissolved in 2 mL of THF and treated with an excess of TBAF. Distribution between a saturated aqueous solution of NH$_4$Cl and Et$_2$O, drying of the combined organic phases and chromatography on silica gel with heptane/EtOAc 2:1 gave 0.17 g (40%) of trans N-(2,2,2-trifluoro-ethyl)-N-[4-(2,2,2-trifluoro-1-hydroxy-1-trifluoromethyl-ethyl)-cyclohexyl]-benzenesulfonamide as a light yellow oil, MS: 486 (M−H)$^−$.

Example 2 trans N-[4-(2,2,2-trifluoro-1-hydroxy-1-trifluoromethyl-ethyl)-cyclohexyl]-benzenesulfonamide 2.1

A solution of 350 mg (0.135 mmol) of 2-(4-amino-phenyl)-1,1,1,3,3,3-hexafluoro-propan-2-ol in 10 mL of AcOH was treated with 100 mg of Pt/C (10%) and hydrogenated at atmospheric pressure under intense stirring for 24 hrs. Filtration and evaporation of the solvent gave 400 mg (91%) of the acetate salt of 2-(4-amino-cyclohexyl)-1,1,1,3,3,3-hexafluoro-propan-2-ol as a light brown solid, MS: 266 (M+H)$^+$.

2.2

A solution of 100 mg (0.37 mmol) of the acetate salt of 2-(4-amino-cyclohexyl)-1,1,1,3,3,3-hexafluoro-propan-2-ol in 5 mL of DMF was treated with 0.2 mL (1.16 mmol) of DIPEA and 0.144 mL (1.1 mmol) of benzenesulfonyl chloride. The mixture was stirred for 1 hr and distributed between a diluted aqueous solution of HCl and Et$_2$O. The combined organic phases were dried over Na$_2$SO$_4$ and the solvent was evaporated. Column chromatography on silica gel with EtOAc/heptane 1:1 gave 90 mg (72%) of N-[4-(2,2,2-trifluoro-1-hydroxy-1-trifluoromethyl-ethyl)-cyclohexyl]-benzenesulfonamide as a pink solid, MS: 404 (M−H)$^−$.

2.3

Chromatography of 50 mg (0.12 mmol) of N-[4-(2,2,2-trifluoro-1-hydroxy-1-trifluoromethyl-ethyl)-cyclohexyl]-benzenesulfonamide on silica gel with EtOAc/heptane 2:1 gave ca. 19 mg (38%) of cis-N-[4-(2,2,2-trifluoro-1-hydroxy-1-trifluoromethyl-ethyl)-cyclohexyl]-benzenesulfonamide and ca. 20 mg (40%) of trans-N-[4-(2,2,2-trifluoro-1-hydroxy-1-trifluoromethyl-ethyl)-cyclohexyl]-benzenesulfonamide as a colorless semisolid, MS: 404 (M−H)$^−$.

Example 3 trans N-benzyl-2,2,2-trifluoro-N-[4-(2,2,2-trifluoro-1-hydroxy-1-trifluoromethyl-ethyl)-cyclohexyl]-acetamide 3.1

A solution of 17 g (78.23 mmol) of the acetate salt of 2-(4-amino-cyclohexyl)-1,1,1,3,3,3-hexafluoro-propan-2-ol (example 2.1) in 250 mL of ethanol was treated with 27.2 mL (196 mmol) of NEt$_3$ and 8.75 mL (86.1 mmol) of benzaldehyde. The mixture was stirred overnight at RT and the solvents evaporated i.v. The brown oil obtained was dissolved in 120 mL of DMF and treated with 8.76 mL (58.7 mmol) of DBU and then dropwise with 9.85 mL (58.7 mmol) of TESCl. The mixture was stirred for 4 hrs at RT and distributed between a saturated aqueous solution of NH$_4$Cl and Et$_2$O. The crude material obtained after drying of the combined organic phases over Na$_2$SO$_4$ and evaporation of the solvent was dissolved in 250 mL of ethanol and treated portionwise with 2.2 g (58.7 mmol) of NaBH$_4$ and stirred for 2 hrs at RT. Evaporation of the solvent, distribution between Et$_2$O and an aqueous solution of NaOH, drying of the combined organic phases over Na$_2$SO$_4$ and chromatography on silica gel with heptane/EtOAc (gradient from 6:1 to 2:1) yielded 3.3 g (14%) of cis benzyl-[4-(2,2,2-trifluoro-1-triethylsilanyloxy-1-trifluoromethyl-ethyl)-cyclohexyl]-amine and 4.7 g (20%) trans benzyl-[4-(2,2,2-trifluoro-1-triethylsilanyloxy-1-trifluoromethyl-ethyl)-cyclohexyl]-amine as a yellow oil, MS: 470 (M+H)$^+$.

3.2

A solution of 100 mg (0.28 mmol) of trans benzyl-[4-(2,2,2-trifluoro-1-triethylsilanyloxy-1-trifluoromethyl-ethyl)-cyclohexyl]-amine (example 2) in 2 mL of CH$_2$Cl$_2$ was treated with 0.1 mL (1.24 mmol) of pyridine and 0.1 mL (0.72 mmol) of trifluoroacetic acid anhydride and stirred at RT overnight. Treatment with and excess of TBAF, stirring for 30 min, and distribution of the mixture between diluted aqueous HCl and Et$_2$O, drying of the combined organic phases over Na$_2$SO$_4$ and evaporation gave ca. 100 mg (79%) of trans N-benzyl-2,2,2-trifluoro-N-[4-(2,2,2-trifluoro-1-hydroxy-1-trifluoromethyl-ethyl)-cyclohexyl]-acetamide as a yellow oil, MS: 452 (M+H)$^+$.

Example 4 trans phenyl-[4-(2,2,2-trifluoro-1-hydroxy-1-trifluoromethyl-ethyl)-cyclohexylamino]-acetic acid ethyl ester A solution of 300 mg (1.0 mmol) of the acetate salt of 2-(4-amino-cyclohexyl)-1,1,1,3,3,3-hexafluoro-propan-2-ol (example 2.1) in 5 mL of EtOH was treated with 227 mg (1.0 mmol) of oxo-phenyl-acetic acid ethyl ester and with 87 mg (1.0 mmol) of sodium cyanoborohydride. The mixture was stirred overnight at RT and distributed between a saturated aqueous solution of NaHCO$_3$ and Et$_2$O. Drying of the combined organic phases over Na$_2$SO$_4$ and chromatography on silica gel with heptane/EtOAc 4:1 yielded ca. 100 mg (25%) of cis phenyl-[4-(2,2,2-trifluoro-1-hydroxy-1-trifluoromethyl-ethyl)-cyclohexylamino]-acetic acid ethyl ester and ca. 100 mg (25%) of trans phenyl-[4-(2,2,2-trifluoro-1-hydroxy-1-trifluoromethyl-ethyl)-cyclohexylamino]-acetic acid ethyl ester as a colorless oil, MS: 428 (M+H)$^+$.

Example 5 trans N-benzyl-N-[4-(2,2,2-trifluoro-1-hydroxy-1-trifluoromethyl-ethyl)-cyclohexyl]-acetamide A solution of 50 mg (0.11 mmol) of trans benzyl-[4-(2,2,2-trifluoro-1-triethylsilanyloxy-1-trifluoromethyl-ethyl)-cyclohexyl]-amine (example 3.1) in 1 mL of CH$_2$Cl$_2$ was treated with 0.1 mL of NEt$_3$, cooled to 0° C. and treated with 0.14 mL (1.97 mmol) of acetylchloride. The mixture was stirred for 30 min and distributed between a saturated aqueous solution of NH$_4$Cl and Et$_2$O. The crude material obtained after drying of the combined organic phases over Na$_2$SO$_4$ and evaporation of the solvent was redissolved in 1 mL of THF, treated with an excess of TBAF and left to stir for 1 hr. Distribution between a saturated aqueous solution of NH$_4$Cl and Et$_2$O, drying of the combined organic phases over Na$_2$SO$_4$, evaporation of the solvent and chromatography on silica gel with EtOAc/heptane 1:1 gave 50 mg (95%) of trans N-benzyl-N-[4-(2,2,2-trifluoro-1-hydroxy-1-trifluoromethyl-ethyl)-cyclohexyl]-acetamide as a colorless viscous oil, MS: 398 (M+H)$^+$.

Example 6 trans N-benzyl-N-[4-(2,2,2-trifluoro-1-hydroxy-1-trifluoromethyl-ethyl)-cyclohexyl]-benzenesulfonamide In analogy to example 5, from trans benzyl-[4-(2,2,2-trifluoro-1-triethylsilanyloxy-1-trifluoromethyl-ethyl)-cyclohexyl]-amine (example 3.1) and benzenesulfonylchloride was prepared trans N-benzyl-N-[4-(2,2,2-trifluoro-1-hydroxy-1-trifluoromethyl-ethyl)-cyclohexyl]-benzenesulfonamide as a colorless oil, MS: 494 (M−H)$^−$.

Example 7 trans 2,4-dimethyl-thiazole-5-sulfonic acid [4-(2,2,2-trifluoro-1-hydroxy-1-trifluoromethyl-ethyl)-cyclohexyl]-amide In analogy to example 5, from trans-4-(2,2,2-trifluoro-1-triethylsilanyloxy-1-trifluoromethyl-ethyl)-cyclohexylamine (example 1.2) and 2,4-dimethyl-1,3-thiazol-5-sulfonylchloride was prepared trans 2,4-dimethyl-thiazole-5-sulfonic acid [4-(2,2,2-trifluoro-1-hydroxy-1-trifluoromethyl-ethyl)-cyclohexyl]-amide as a yellow oil, MS: 441 (M+H)$^+$.

Example 8 trans 1,2-dimethyl-1H-imidazole-4-sulfonic acid [4-(2,2,2-trifluoro-1-hydroxy-1-trifluoromethyl-ethyl)-cyclohexyl]-amide In analogy to example 5, from trans 4-(2,2,2-trifluoro-1-triethylsilanyloxy-1-trifluoromethyl-ethyl)-cyclohexylamine (example 1.2) and 1,2-dimethyl-1H-imidazole-4-sulfonylchloride was prepared trans 1,2-dimethyl-1H-imidazole-4-sulfonic acid [4-(2,2,2-trifluoro-1-hydroxy-1-trifluoromethyl-ethyl)-cyclohexyl]-amide as an off-white solid, MS: 424 (M+H)$^+$.

Example 9 trans 1,2-dimethyl-1H-imidazole-4-sulfonic acid (2,2,2-trifluoro-ethyl)-[4-(2,2,2-trifluoro-1-hydroxy-1-trifluoromethyl-ethyl)-cyclohexyl]-amide 9.1

In analogy to example 1.3, from trans-4-(2,2,2-trifluoro-1-triethylsilanyloxy-1-trifluoromethyl-ethyl)-cyclohexylamine and 1,2-dimethyl-1H-imidazole-4-sulfonylchloride was prepared trans 1,2-dimethyl-1H-imidazole-4-sulfonic acid [4-(2,2,2-trifluoro-1-triethylsilanyloxy-1-trifluoromethyl-ethyl)-cyclohexyl]-amide, as a white solid, MS: 538 (M+H)$^+$.

9.2

In analogy to example 1.4, from trans 1,2-dimethyl-1H-imidazole-4-sulfonic acid [4-(2,2,2-trifluoro-1-triethylsilanyloxy-1-trifluoromethyl-ethyl)-cyclohexyl]-amide and trifluoro-methanesulfonic acid 2,2,2-trifluoro-ethyl ester was prepared trans 1,2-dimethyl-1H-imidazole-4-sulfonic acid (2,2,2-trifluoro-ethyl)-[4-(2,2,2-trifluoro-1-hydroxy-1-trifluoromethyl-ethyl)-cyclohexyl]-amide as a light brown solid, MS: 506 (M+H)$^+$.

Example 10 trans 1,2-dimethyl-1H-imidazole-4-sulfonic acid ethyl-[4-(2,2,2-trifluoro-1-hydroxy-1-trifluoromethyl-ethyl)-cyclohexyl]-amide 10.1

A solution of 150 mg (0.28 mmol) of trans 1,2-dimethyl-1H-imidazole-4-sulfonic acid [4-(2,2,2-trifluoro-1-triethylsilanyloxy-1-trifluoromethyl-ethyl)-cyclohexyl]-amide (example 9.1) in 1 mL of DMF was treated with 0.66 mL (0.44 mmol) of DBU, stirred for 15 min and treated with 0.9 mL (0.58 mmol) of ethyliodide. The mixture was stirred at 60° C. for 4 hrs and distributed between a saturated aqueous solution of $NH_4Cl$ and $Et_2O$. Drying of the combined organic phases over $Na_2SO_4$ and evaporation of the solvent gave 150 mg (95%) of trans 1,2-dimethyl-1H-imidazole-4-sulfonic acid ethyl-[4-(2,2,2-trifluoro-1-triethylsilanyloxy-1-trifluoromethyl-ethyl)-cyclohexyl]-amide as a light yellow liquid, MS: 566 $(M+H)^+$.

10.2

A solution of 130 mg (0.23 mmol) of trans 1,2-dimethyl-1H-imidazole-4-sulfonic acid ethyl-[4-(2,2,2-trifluoro-1-triethylsilanyloxy-1-trifluoromethyl-ethyl)-cyclohexyl]-amide in 2 mL of THF was treated with an excess of TBAF and stirred for 2 hrs at RT. Distribution between a saturated aqueous solution of $NH_4Cl$ and $Et_2O$, drying of the combined organic phases, evaporation of the solvent and column chromatography on silica gel with EtOAc/heptane 1:1 gave 42 mg (25%) of trans 1,2-dimethyl-1H-imidazole-4-sulfonic acid ethyl-[4-(2,2,2-trifluoro-1-hydroxy-1-trifluoromethyl-ethyl)-cyclohexyl]-amide as a yellow viscous oil, MS: 452 $(M+H)^+$.

Example 11 trans 4-methyl-2-propyl-thiazole-5-sulfonic acid ethyl-[4-(2,2,2-trifluoro-1-hydroxy-1-trifluoromethyl-ethyl)-cyclohexyl]-amide 11.1

In analogy to example 1.3, from trans-4-(2,2,2-trifluoro-1-triethylsilanyloxy-1-trifluoromethyl-ethyl)-cyclohexylamine (example 1.2) and 2,4-dimethyl-1,3-thiazol-5-sulfonylchloride was prepared trans 2,4-dimethyl-thiazole-5-sulfonic acid [4-(2,2,2-trifluoro-1-triethylsilanyloxy-1-trifluoromethyl-ethyl)-cyclohexyl]-amide as a white solid, MS: 555 $(M+H)^+$.

11.2

A solution of 200 mg (0.36 mmol) of trans 2,4-dimethyl-thiazole-5-sulfonic acid [4-(2,2,2-trifluoro-1-triethylsilanyloxy-1-trifluoromethyl-ethyl)-cyclohexyl]-amide in 5 mL of THF was cooled to −78° C. and treated dropwise with 0.25 mL of a 1.6 M solution of nBuLi in hexane. The solution was warmed to −30° C., treated with 1 mL (1.2 mmol) of ethyliodide, allowed to reach RT and then refluxed for 2 hrs. Distribution between a saturated aqueous solution of $NH_4Cl$ and $Et_2O$, drying of the combined organic phases over $Na_2SO_4$ and evaporation of the solvent gave a residue that was redissolved in THF and treated with an excess of TBAF. Distribution between a saturated aqueous solution of $NH_4Cl$ and $Et_2O$, drying of the combined organic phases over $Na_2SO_4$, evaporation of the solvent and chromatography on silicagel with heptane/EtOAc 2:1 yielded 20 mg (11%) of trans 4-methyl-2-propyl-thiazole-5-sulfonic acid ethyl-[4-(2,2,2-trifluoro-1-hydroxy-1-trifluoromethyl-ethyl)-cyclohexyl]-amide as a yellow oil, MS: 497 $(M+H)^+$.

Example 12 trans 2,4-dimethyl-thiazole-5-sulfonic acid (2,2,2-trifluoro-ethyl)-[4-(2,2,2-trifluoro-1-hydroxy-1-trifluoromethyl-ethyl)-cyclohexyl]-amide In analogy to example 1.4, from trans 2,4-dimethyl-thiazole-5-sulfonic acid [4-(2,2,2-trifluoro-1-triethylsilanyloxy-1-trifluoromethyl-ethyl)-cyclohexyl]-amide (example 11.1) and trifluoro-methanesulfonic acid 2,2,2-trifluoro-ethyl ester was prepared trans 2,4-dimethyl-thiazole-5-sulfonic acid (2,2,2-trifluoro-ethyl)-[4-(2,2,2-trifluoro-1-hydroxy-1-trifluoromethyl-ethyl)-cyclohexyl]-amide as a yellow viscous oil, MS: 523 $(M+H)^+$.

Example 13 trans 2,4-dimethyl-thiazole-5-sulfonic acid cyclopropylmethyl-[4-(2,2,2-trifluoro-1-hydroxy-1-trifluoromethyl-ethyl)-cyclohexyl]-amide In analogy to example 10, from trans 2,4-dimethyl-thiazole-5-sulfonic acid [4-(2,2,2-trifluoro-1-triethylsilanyloxy-1-trifluoromethyl-ethyl)-cyclohexyl]-amide (example 11.1) and bromomethylcyclopropane was prepared trans 2,4-dimethyl-thiazole-5-sulfonic acid cyclopropylmethyl-[4-(2,2,2-trifluoro-1-hydroxy-1-trifluoromethyl-ethyl)-cyclohexyl]-amide as a yellow gum, MS: 495 $(M+H)^+$.

Example 14 trans 2,4-dimethyl-thiazole-5-sulfonic acid ethyl-[4-(2,2,2-trifluoro-1-hydroxy-1-trifluoromethyl-ethyl)-cyclohexyl]-amide In analogy to example 10, from trans 2,4-dimethyl-thiazole-5-sulfonic acid [4-(2,2,2-trifluoro-1-triethylsilanyloxy-1-trifluoromethyl-ethyl)-cyclohexyl]-amide (example 11.1) and ethyliodide was prepared trans 2,4-dimethyl-thiazole-5-sulfonic acid ethyl-[4-(2,2,2-trifluoro-1-hydroxy-1-trifluoromethyl-ethyl)-cyclohexyl]-amide as a yellow oil, MS: 469 $(M+H)^+$.

Example 15 trans N-cyclopropylmethyl-N-[4-(2,2,2-trifluoro-1-hydroxy-1-trifluoromethyl-ethyl)-cyclohexyl]-benzenesulfonamide A solution of 500 mg (0.89 mmol) of trans N-[4-(2,2,2-trifluoro-1-triethylsilanyloxy-1-trifluoromethyl-ethyl)-cyclohexyl]-benzenesulfonamide (example 1.3) in 10 mL of THF was cooled to −78° C. and treated dropwise with 0.72 mL of a 1.6 M BuLi solution in hexane. The solution was warmed to −40° C. within 30 min, treated with 0.43 mL (4.45 mmol) of bromomethylcyclopropane, allowed to reach RT and then refluxed overnight. An excess of TBAF was added and the mixture was stirred for an additional hour. Distribution of the crude mixture between a saturated aqueous solution of $NH_4Cl$ and $Et_2O$, drying of the combined organic phases over Na$_2$SO$_4$, evaporation and chromatography on silica gel with CH$_2$Cl$_2$ gave 200 mg (49%) of trans N-cyclopropylmethyl-N-[4-(2,2,2-trifluoro-1-hydroxy-1-trifluoromethyl-ethyl)-cyclohexyl]-benzenesulfonamide, as a colorless viscous oil, MS: 460 (M+H)$^+$.

Example 16 trans N-ethyl-N-[4-(2,2,2-trifluoro-1-hydroxy-1-trifluoromethyl-ethyl)-cyclohexyl]-benzenesulfonamide In analogy to example 10, from trans N-[4-(2,2,2-trifluoro-1-triethylsilanyloxy-1-trifluoromethyl-ethyl)-cyclohexyl]-benzenesulfonamide (example 1.3) and ethyliodide was prepared trans N-ethyl-N-[4-(2,2,2-trifluoro-1-hydroxy-1-trifluoromethyl-ethyl)-cyclohexyl]-benzenesulfonamide as a colorless oil, MS: 434 (M+H)$^+$.

Example 17 trans 5-chloro-1,4-dimethyl-1H-pyrazole-3-sulfonic acid (2,2,2-trifluoro-ethyl)-[4-(2,2,2-trifluoro-1-hydroxy-1-trifluoromethyl-ethyl)-cyclohexyl]-amide 17.1
In analogy to example 1.3, from trans-4-(2,2,2-trifluoro-1-triethylsilanyloxy-1-trifluoromethyl-ethyl)-cyclohexylamine and 5-chloro-1,3-dimethylpyrazol-4-sulfonylchloride was prepared trans 5-chloro-1,4-dimethyl-1H-pyrazole-3-sulfonic acid [4-(2,2,2-trifluoro-1-triethylsilanyloxy-1-trifluoromethyl-ethyl)-cyclohexyl]-amide as an off-white amorphous solid, MS: 528 (M+H)$^+$.

17.2
In analogy to example 10, from trans 5-chloro-1,4-dimethyl-1H-pyrazole-3-sulfonic acid [4-(2,2,2-trifluoro-1-triethylsilanyloxy-1-trifluoromethyl-ethyl)-cyclohexyl]-amide and trifluoro-methanesulfonic acid 2,2,2-trifluoro-ethyl ester was prepared trans 5-chloro-1,4-dimethyl-1H-pyrazole-3-sulfonic acid (2,2,2-trifluoro-ethyl)-[4-(2,2,2-trifluoro-1-hydroxy-1-trifluoromethyl-ethyl)-cyclohexyl]-amide as a light yellow oil, MS: 540 ((M+H)$^+$, 1 Cl).

Example 18 trans 5-chloro-1,4-dimethyl-1H-pyrazole-3-sulfonic acid [4-(2,2,2-trifluoro-1-hydroxy-1-trifluoromethyl-ethyl)-cyclohexyl]-amide In analogy to example 10.2, from trans 5-chloro-1,4-dimethyl-1H-pyrazole-3-sulfonic acid [4-(2,2,2-trifluoro-1-triethylsilanyloxy-1-trifluoromethyl-ethyl)-cyclohexyl]-amide (example 17.1) was prepared trans 5-chloro-1,4-dimethyl-1H-pyrazole-3-sulfonic acid [4-(2,2,2-trifluoro-1-hydroxy-1-trifluoromethyl-ethyl)-cyclohexyl]-amide an off-white semisolid, MS: 458 ((M+H)$^+$, 1Cl)

Example 19 trans 2-[4-(benzyl-ethyl-amino)-cyclohexyl]-1,1,1,3,3,3-hexafluoro-propan-2-ol

A solution of 200 mg (0.43 mmol) of trans benzyl-[4-(2,2,2-trifluoro-1-triethylsilanyloxy-1-trifluoromethyl-ethyl)-cyclohexyl]-amine (example 3.1) in 2 mL of pyridine was treated with 0.05 mL of acetic acid anhydride (0.51 mmol), stirred overnight at RT and distributed between a saturated aqueous solution of NH$_4$Cl and Et$_2$O. After drying of the combined organic phases over Na$_2$SO$_4$ and evaporation of the solvent, the residue was dissolved in 3.5 mL of THF and treated with 0.86 mL of a 1M BH$_3$-solution in THF. The mixture was stirred at RT for 2 hrs, and the solvent evaporated. The residue was redissolved in THF treated with an excess of TBAF and solution was stirred for 2 hrs. Evaporation of the solvent and chromatography on silica gel with hexane/EtOAc 4:1 gave 64 mg (39%) of trans 2-[4-(benzyl-ethyl-amino)-cyclohexyl]-1,1,1,3,3,3-hexafluoro-propan-2-ol as a light yellow oil, MS: 384 (M+H)$^+$.

Example 20 trans 2-[4-(benzyl-propyl-amino)-cyclohexyl]-1,1,1,3,3,3-hexafluoro-propan-2-ol

In analogy to example 19, from, trans benzyl-[4-(2,2,2-trifluoro-1-triethylsilanyloxy-1-trifluoromethyl-ethyl)-cyclohexyl]-amine (example 3.1) and propionylchloride was prepared trans 2-[4-(benzyl-propyl-amino)-cyclohexyl]-1,1,1,3,3,3-hexafluoro-propan-2-ol as a colorless oil, MS: 398 (M+H)$^+$.

Example 21 trans 2-[4-(benzyl-cyclopropylmethyl-amino)-cyclohexyl]-1,1,1,3,3,3-hexafluoro-propan-2-ol In analogy to example 19, from transbenzyl-[4-(2,2,2-trifluoro-1-triethylsilanyloxy-1-trifluoromethyl-ethyl)-cyclohexyl]-amine (example 3.1) and cyclopropylcarbonylchloride was prepared trans 2-[4-(benzyl-cyclopropylmethyl-amino)-cyclohexyl]-1,1,1,3,3,3-hexafluoro-propan-2-ol as a colorless oil, MS: 310 (M+H)$^+$.

Example 22 trans N-benzyl-N-[4-(2,2,2-trifluoro-1-hydroxy-1-trifluoromethyl-ethyl)-cyclohexyl]-propionamide In analogy to example 5, from transbenzyl-[4-(2,2,2-trifluoro-1-triethylsilanyloxy-1-trifluoromethyl-ethyl)-cyclohexyl]-amine (example 3.1) and propionylchloride was prepared trans N-benzyl-N-[4-(2,2,2-trifluoro-1-hydroxy-1-trifluoromethyl-ethyl)-cyclohexyl]-propionamide as a light yellow oil, MS: 412 (M+H)$^+$.

Example 23 trans cyclopropanecarboxylic acid benzyl-[4-(2,2,2-trifluoro-1-hydroxy-1-trifluoromethyl-ethyl)-cyclohexyl]-amide In analogy to example 5, from transbenzyl-[4-(2,2,2-trifluoro-1-triethylsilanyloxy-1-trifluoromethyl-ethyl)-cyclohexyl]-amine (example 3.1) and cyclopropylcarbonylchloride was prepared trans cyclopropanecarboxylic acid benzyl-[4-(2,2,2-trifluoro-1-hydroxy-1-trifluoromethyl-ethyl)-cyclohexyl]-amide as a light yellow oil, MS: 424 (M+H)$^+$.

Example 24 trans N-cyclopropylmethyl-N-[4-(2,2,2-trifluoro-1-hydroxy-1-trifluoromethyl-ethyl)-cyclohexyl]-benzamide 24.1

A solution of 930 mg (1.73 mmol) of trans benzyl-[4-(2,2,2-trifluoro-1-triethylsilanyloxy-1-trifluoromethyl-ethyl)-cyclohexyl]-amine (example 3.1) in 2 mL of $CH_2Cl_2$ was treated with 0.6 mL (3.5 mmol) of DIPEA and 0.23 mL (2.56 mmol) of cyclopropylcarbonylchloride. The mixture was stirred at RT overnight and distributed between a saturated aqueous solution of $NH_4Cl$ and $Et_2O$. The combined organic phases were dried over $Na_2SO_4$, and the solvent was evaporated. The crude material obtained was dissolved in 10 mL of THF, treated with 3.46 mL of a 1M $BH_3$-solution in THF and refluxed for 6 hrs. Distribution between a diluted aqueous solution of NaOH and $Et_2O$, drying of the combined organic phases over $Na_2SO_4$ and evaporation of the solvent gave 1 g of crude trans benzyl-cyclopropylmethyl-[4-(2,2,2-trifluoro-1-triethylsilanyloxy-1-trifluoromethyl-ethyl)-cyclohexyl]-amine as a yellow oil, MS: 524 $(M+H)^+$.

24.2

1 g (ca 2.0 mmol) of crude trans benzyl-cyclopropylmethyl-[4-(2,2,2-trifluoro-1-triethylsilanyloxy-1-trifluoromethyl-ethyl)-cyclohexyl]-amine was dissolved in 50 mL of acetic acid, treated with 300 mg of Pd/C (10%) and hydrogenated overnight at atmospheric pressure under intense stirring. Filtration and evaporation of the solvent gave 775 mg (ca 82%) of crude trans cyclopropylmethyl-[4-(2,2,2-trifluoro-1-triethylsilanyloxy-1-trifluoromethyl-ethyl)-cyclohexyl]-amine as a yellow oil, MS: 434 $(M+H)^+$.

24.3

A solution of 50 mg (0.12 mmol) of trans cyclopropylmethyl-[4-(2,2,2-trifluoro-1-triethylsilanyloxy-1-trifluoromethyl-ethyl)-cyclohexyl]-amine in 3 mL of a 1:2-mixture of THF and 1,2-dichloroethane was treated with 0.03 mL (0.23 mmol) of $NEt_3$ and 0.02 mL (0.14 mmol) of benzoylchloride. The mixture was stirred at RT for 2 hrs and distributed between a saturated aqueous solution of $NH_4Cl$ and $Et_2O$. After drying of the combined organic phases over $Na_2SO_4$ and evaporation of the solvent the residue was redissolved in 2 mL of THF, treated with an excess of TBAF and distributed between a saturated aqueous solution of $NH_4Cl$ and $Et_2O$. Drying of the combined organic phases over $Na_2SO_4$ and column chromatography on silica gel with heptane/EtOAc 2:1 gave 35 mg (72%) of trans N-cyclopropylmethyl-N-[4-(2,2,2-trifluoro-1-hydroxy-1-trifluoromethyl-ethyl)-cyclohexyl]-benzamide as a white solid, MS: 424, $(M+H)^+$.

Example 25 trans N-cyclopropylmethyl-2-phenyl-N-[4-(2,2,2-trifluoro-1-hydroxy-1-trifluoromethyl-ethyl)-cyclohexyl]-acetamide In analogy to example 24.3, from trans cyclopropylmethyl-[4-(2,2,2-trifluoro-1-triethylsilanyloxy-1-trifluoromethyl-ethyl)-cyclohexyl]-amine (example 24.2) and phenylacetylchloride was prepared trans N-cyclopropylmethyl-2-phenyl-N-[4-(2,2,2-trifluoro-1-hydroxy-1-trifluoromethyl-ethyl)-cyclohexyl]-acetamide as a light brown oil, MS: 438 $(M+H)^+$.

Example 26 trans cyclopropylmethyl-[4-(2,2,2-trifluoro-1-hydroxy-1-trifluoromethyl-ethyl)-cyclohexyl]-carbamic acid phenyl ester In analogy to example 24.3, from trans cyclopropylmethyl-[4-(2,2,2-trifluoro-1-triethylsilanyloxy-1-trifluoromethyl-ethyl)-cyclohexyl]-amine (example 24.2) and phenyl chloroformate was prepared trans cyclopropylmethyl-[4-(2,2,2-trifluoro-1-hydroxy-1-trifluoromethyl-ethyl)-cyclohexyl]-carbamic acid phenyl ester as a light brown oil, MS: 440 $(M+H)^+$.

Example 27 trans cyclopropylmethyl-[4-(2,2,2-trifluoro-1-hydroxy-1-trifluoromethyl-ethyl)-cyclohexyl]-carbamic acid benzyl ester In analogy to example 24.3, from trans cyclopropylmethyl-[4-(2,2,2-trifluoro-1-triethylsilanyloxy-1-trifluoromethyl-ethyl)-cyclohexyl]-amine (example 24.2) and benzyl chloroformate was prepared trans cyclopropylmethyl-[4-(2,2,2-trifluoro-1-hydroxy-1-trifluoromethyl-ethyl)-cyclohexyl]-carbamic acid benzylester as a light brown oil, MS: 454 $(M+H)^+$.

Example 28

(rac) trans 2-{4-[cyclopropylmethyl-(2-hydroxy-2-phenyl-ethyl)-amino]-cyclohexyl}-1,1,1,3,3,3-hexafluoro-propan-2-ol 28.1

A solution of 100 mg (0.23 mmol) of trans cyclopropylmethyl-[4-(2,2,2-trifluoro-1-triethylsilanyloxy-1-trifluoromethyl-ethyl)-cyclohexyl]-amine (example 24.2) in 0.5 mL of acetonitrile was treated with 41 mg (0.38 mmol) of lithiumperchlorate and 46 mg (0.38 mmol) of (rac) phenyl-ethylenoxide. The mixture was stirred in a sealed tube at 80° C. for 6 hrs and distributed between a saturated aqueous solution of $NH_4Cl$ and $Et_2O$. Drying of the combined organic phases over $Na_2SO_4$, evaporation of the solvent and column chromatography on silica gel with heptane/EtOAc 1:1 gave 52 mg (49%) of (rac) trans 2-{cyclopropylmethyl-[4-(2,2,2-trifluoro-1-triethylsilanyloxy-1-trifluoromethyl-ethyl)-cyclohexyl]-amino}-1-phenyl-ethanol as a colorless oil, MS: 554 $(M+H)^+$.

28.2

In analogy to example 10.2, from (rac) trans 2-{cyclopropylmethyl-[4-(2,2,2-trifluoro-1-triethylsilanyloxy-1-trifluoromethyl-ethyl)-cyclohexyl]-amino}-1-phenyl-ethanol was prepared (rac) trans 2-{4-[cydopropylmethyl-(2-hydroxy-2-phenyl-ethyl)-amino]-cyclohexyl}-1,1,1,3,3,3-hexafluoro-propan-2-ol, light yellow semisolid, MS: 440 $(M+H)^+$.

Example 29 trans Benzyl-N-[4-(2,2,2-trifluoro-1-hydroxy-1-trifluoromethyl-ethyl)-cyclohexyl]-sulfonamide 29.1

In analogy to example 1.3, from trans-4-(2,2,2-trifluoro-1-triethylsilanyloxy-1-trifluoromethyl-ethyl)-cyclohexylamine and phenylmethanesulfonylchloride was prepared trans benzyl-N-[4-(2,2,2-trifluoro-1-triethylsilanyloxy-1-trifluoromethyl-ethyl)-cyclohexyl]-sulfonamide as a yellow solid, MS: 534 (M+H)$^+$.

29.2

In analogy to example 10.2, from trans benzyl-N-[4-(2,2,2-trifluoro-1-triethylsilanyloxy-1-trifluoromethyl-ethyl)-cyclohexyl]-sulfonamide was prepared trans benzyl-N-[4-(2,2,2-trifluoro-1-hydroxy-1-trifluoromethyl-ethyl)-cyclohexyl]-sulfonamide, as a light brown gum, MS: 420 (M+H)$^+$.

Example 30 trans Benzyl-N-(2,2,2-trifluoro-ethyl)-N-[4-(2,2,2-trifluoro-1-hydroxy-1-trifluoromethyl-ethyl)-cyclohexyl]-sulfonamide 30.1

A solution of 200 mg (0.37 mmol) of trans benzyl-N-[4-(2,2,2-trifluoro-1-triethylsilanyloxy-1-trifluoromethyl-ethyl)-cyclohexyl]-sulfonamide (example 29.1) in 2 mL of THF was cooled to −78° C. and treated dropwise with a 0.4 mL of a 1M lithium-bis-(trimethylsilyl)amide-solution in THF. The mixture was warmed to −40° C., treated with 609 mg (2.6 mmol) of trifluoro-methanesulfonic acid 2,2,2-trifluoro-ethyl ester and allowed to reach RT. After 4 hours of refluxing, the mixture was cooled to RT and distributed between a saturated aqueous solution of NH$_4$Cl and Et$_2$O. The combined organic phases were dried over Na$_2$SO$_4$ and the solvent was evaporated. Chromatography on silica gel with heptane/EtOAc 9:1 gave 140 mg (61%) of trans benzyl-N-(2,2,2-trifluoro-ethyl)-N-[4-(2,2,2-trifluoro-1-triethylsilanyloxy-1-trifluoromethyl-ethyl)-cyclohexyl]-sulfonamide as a light yellow oil, MS: 614 (M−H)$^-$.

30.2

In analogy to example 10.2, from trans benzyl-N-(2,2,2-trifluoro-ethyl)-N-[4-(2,2,2-trifluoro-1-triethylsilanyloxy-1-trifluoromethyl-ethyl)-cyclohexyl]-sulfonamide was prepared trans benzyl-N-(2,2,2-trifluoro-ethyl)-N-[4-(2,2,2-trifluoro-1-hydroxy-1-trifluoromethyl-ethyl)-cyclohexyl]-sulfonamide as an off-white foam, MS: 502 (M+H)$^+$.

Example 31

(rac) trans 1-phenyl-ethanesulfonic acid (2,2,2-trifluoro-ethyl)-[4-(2,2,2-trifluoro-1-hydroxy-1-trifluoromethyl-ethyl)-cyclohexyl]-amide 31.1

A solution of 128 mg (0.21 mmol) of trans benzyl-N-[4-(2,2,2-trifluoro-1-triethylsilanyloxy-1-trifluoromethyl-ethyl)-cyclohexyl]-sulfonamide (example 30.1) in 2 mL of THF was cooled to −78° C. and treated dropwise with 0.42 mL of a 1M lithium-bis-(trimethylsilyl)amide solution in THF and allowed to reach −40°. After addition of 0.13 mL (2.1 mmol) of iodomethane the mixture was stirred at RT during 4 hrs and distributed between a saturated aqueous solution of NH$_4$Cl and Et$_2$O. The combined organic phases were dried over Na$_2$SO$_4$ and the solvent was evaporated to yield 130 mg (98%) of crude (rac) trans 1-phenyl-ethanesulfonic acid (2,2,2-trifluoro-ethyl)-[4-(2,2,2-trifluoro-1-triethylsilanyloxy-1-trifluoromethyl-ethyl)-cyclohexyl]-amide as a light yellow oil, MS: 648 (M+NH$_4$)$^+$.

31.2

A solution of 30 mg of (2,2,2-trifluoro-ethyl)-[4-(2,2,2-trifluoro-1-triethylsilanyloxy-1-trifluoromethyl-ethyl)-cyclohexyl]-amide in methanol was treated with 0.12 mL of a 2 M NaOMe-solution in MeOH. Distribution between a saturated aqueous solution of NH$_4$Cl and Et$_2$O and column chromatography with heptane/EtOAc 2:1 gave 18 mg (73%) of (rac) trans 1-phenyl-ethanesulfonic acid (2,2,2-trifluoro-ethyl)-[4-(2,2,2-trifluoro-1-hydroxy-1-trifluoromethyl-ethyl)-cyclohexyl]-amide, colorless oil, MS: 514 (M−H)$^-$.

Example 32 trans 2-phenyl-propane-2-sulfonic acid (2,2,2-trifluoro-ethyl)-[4-(2,2,2-trifluoro-1-hydroxy-1-trifluoromethyl-ethyl)-cyclohexyl]-amide A solution of 100 mg (0.16 mmol) of 1-phenyl-ethanesulfonic acid (2,2,2-trifluoro-ethyl)-[4-(2,2,2-trifluoro-1-triethylsilanyloxy-1-trifluoromethyl-ethyl)-cyclohexyl]-amide (example 31.1) in THF was cooled to −78° C. and treated dropwise with 0.17 mL of a 1M solution of lithium bis (trimethylsilyl)amide in THF. The mixture was warmed to 0° C. and treated with 0.22 mL (0.35 mmol) of iodomethane, allowed to reach RT and then refluxed for 4 hrs. Distribution of the mixture between a saturated aqueous solution of NH$_4$Cl and Et$_2$O, drying of the combined organic phases over Na$_2$SO$_4$ and evaporation of the solvent gave a residue that was dissolved in 2 mL of MeOH and treated with 0.5 mL of a 2M solution of NaOMe. Distribution of this solution between a saturated aqueous solution of NH$_4$Cl and Et$_2$O, drying of the combined organic phases over Na$_2$SO$_4$, vaporation and column chromatography on silica gel with CH$_2$Cl$_2$/heptane 1:2 gave 6 mg (7%) of trans 2-phenyl-propane-2-sulfonic acid (2,2,2-trifluoro-ethyl)-[4-(2,2,2-trifluoro-1-hydroxy-1-trifluoromethyl-ethyl)-cyclohexyl]-amide as a white gum, MS: 528 (M−H)$^-$.

Example 33

(rac) trans 1,2-diphenyl-ethanesulfonic acid (2,2,2-trifluoro-ethyl)-[4-(2,2,2-trifluoro-1-hydroxy-1-trifluoromethyl-ethyl)-cyclohexyl]-amide A solution of 50 mg (0.08 mmol) of trans benzyl-N-(2,2,2-trifluoro-ethyl)-N-[4-(2,2,2-trifluoro-1-triethylsilanyloxy-1-trifluoromethyl-ethyl)-cyclohexyl]-sulfonamide (example 30.1) in 0.5 mL of THF was cooled to −78° C. and treated with 0.11 mL of a 1M solution lithium bis(trimethylsilyl)amide in THF. The mixture was allowed to reach ca −5° C. within 30 min and treated with 0.11 mL (0.1 mmol) of benzylbromide. The mixture was stirred overnight and distributed between diluted aqueous solution of HCl and Et$_2$O. The combined organic phases were dried over Na$_2$SO$_4$ and the solvent was evaporated. The residue was redissolved in MeOH and treated with 0.5 mL of a 2M solution of NaOMe in MeOH. Distribution of this solution between a saturated aqueous solution of NH$_4$Cl and Et$_2$O, drying of the combined organic phases over Na$_2$SO$_4$, evaporation and column chromatography on silica gel with heptane/EtOAc 4:1 gave 50 mg (76%) of (rac) trans 1,2-diphenyl-ethanesulfonic acid (2,2,2-trifluoro-ethyl)-[4-(2,2,2-trifluoro-1-hydroxy-1-trifluoromethyl-ethyl)-cyclohexyl]-amide as a colorless foam, MS: 590 (M−H)$^-$.

Example 34

(rac) trans 3-(2-phenyl-2-{(2,2,2-trifluoro-ethyl)-[4-(2,2,2-trifluoro-1-hydroxy-1-trifluoromethyl-ethyl)-cyclohexyl]-sulfamoyl}-ethyl)-benzoic acid methyl ester In analogy to example 33, from benzyl-N-(2,2,2-trifluoro-ethyl)-N-[4-(2,2,2-trifluoro-1-triethylsilanyloxy-1-trifluoromethyl-ethyl)-cyclohexyl]-sulfonamide (example 30.1) and methyl-3-(bromomethyl)benzoate instead of benzylbromide was prepared (rac) trans 3-(2-phenyl-2-{(2,2,2-trifluoro-ethyl)-[4-(2,2,2-trifluoro-1-hydroxy-1-trifluoromethyl-ethyl)-cyclohexyl]-sulfamoyl}-ethyl)-benzoic acid methyl ester, colorless oil, MS: 648 (M−H)$^-$.

Example 35 cis N-Ethyl-N-[4-(2,2,2-trifluoro-1-hydroxy-1-trifluoromethyl-ethyl)-cyclohexyl]-benzenesulfonamide 35.1

In analogy to example 1.3, from cis 4-(2,2,2-trifluoro-1-triethylsilanyloxy-1-trifluoromethyl-ethyl)-cyclohexylamine (example 1.2) was prepared cis N-[4-(2,2,2-trifluoro-1-triethylsilanyloxy-1-trifluoromethyl-ethyl)-cyclohexyl]-benzenesulfonamide as a colorless oil, MS: 518 (M−H)$^-$ 35.2

In analogy to example 10, from cis N-[4-(2,2,2-trifluoro-1-triethylsilanyloxy-1-trifluoromethyl-ethyl)-cyclohexyl]-benzenesulfonamide and ethyliodide was prepared cis N-ethyl-N-[4-(2,2,2-trifluoro-1-hydroxy-1-trifluoromethyl-ethyl)-cyclohexyl]-benzenesulfonamide as a light yellow viscous oil, MS: 434 (M+H)$^+$.

Example 36

Film coated tablets containing the following ingredients can be manufactured in a conventional manner:

Ingredients Per Tablet

| Kernel: | | |
|---|---|---|
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example 37

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 38

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example 39

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg |
| | (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 40

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesiumstearate and the flavouring additives and filled into sachets.

Example 41

The following tests were carried out in order to determine the activity of the compounds of the present invention. Background information on the performed assays can be found in: Nichols J S et al. "Development of a scintillation proximity assay for peroxisome proliferator-activated receptor gamma ligand binding domain", Anal Biochem. 1998, 257: 112-119.

Mammalian expression vectors were constructed to express full-length human LXR alpha and LXR beta. Bacterial expression vectors were constructed to produce glutathione-s-transferase (GST) fused to the ligand binding domains (LBD) of human LXR alpha (aa 164 to 447) and human LXR beta (aa 155 to 460). To accomplish this, the portions of the sequences encoding the LBDs were amplified from full-length clones by PCR and then subcloned into the plasmid vectors. Final clones were verified by DNA sequence analysis (Willy et al., Genes Dev. 1995, 9:1033-45; Song et al., Proc Natl Acad Sci USA. 1994, 91:10809-13).

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al).

Radioligand Binding Assay

LXR alpha and LXR beta receptor binding were assayed in buffer consisting of 50 mM HEPES, pH 7.4, 10 mM NaCl, 5 mM $MgCl_2$. For each 96-well reaction, 500 ng of GST-LXRα-LBD or 700 ng of GST-LXR beta-LBD fusion proteins were bound to 80 μg or 40 μg SPA beads (Pharmacia Amersham) respectively, in a final volume of 50 μl by shaking. The resulting slurry was incubated for 1 h at RT and centrifuged for 2 min at 1300×g. The supernatant containing unbound protein was removed, and the semi-dry pellet containing the receptor-coated beads was re-suspended in 50 μl of buffer. Radioligand (eg. 100,000 dpm of (N-(2,2,2-trifluoroethyl)-N-[4-(2,2,2-trifluoro-1-hydroxy-1-trifluoromethylethyl)-phenyl]-benzenesulfonamide)) was added, and the reaction incubated at RT for 1 h in the presence of test compounds, and then scintillation proximity counting was performed. All binding assays were performed in 96-well plates and the amount of bound ligand was measured on a Packard TopCount using OptiPlates (Packard). Dose response curves were measured within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95%$O_2$:5% $CO_2$ atmosphere. Cells were seeded in 6-well plates at a density of $10^5$ Cells/well and then batch-transfected with either the full-length-LXRα or full-length-LXRβ expression plasmids plus a reporter plasmid expressing luceriferase under the control of LXR response elements. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays (EC50) of 1 nM to 100 μM, preferably 1 nM to 10 μM, more preferably 1 nM to 1 μM.

For example, the following compounds showed the following IC50 values in the binding assay:

| Example | LXRalpha Binding $IC_{50}$ [μmol/l] | LXRbeta Binding $IC_{50}$ [μmol/l] |
|---|---|---|
| 1 | 0.02 | 0.07 |
| 17 | 1.5 | 1.4 |

It is understood that the invention is not limited to the particular embodiments of the invention described above, as variations of the particular embodiments may be made and still fall within the scope of the appended claims.

What is claimed is:

1. A compound of formula (I)

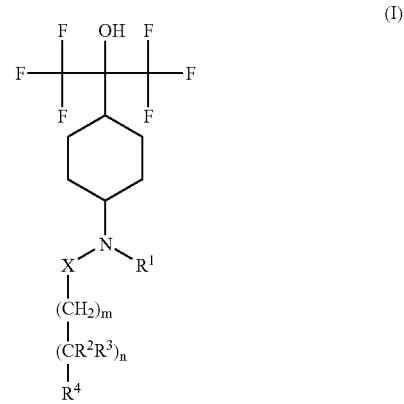

wherein
R[1] is hydrogen, lower-alkyl, fluoro-lower-alkyl, lower-alkyl-carbonyl, fluoro-lower-alkyl-carbonyl, aryl-lower-alkyl, cycloalkyl-lower-alkyl, cycloalkyl-carbonyl or cycloalkyl-lower-alkyl-carbonyl;

R² is hydrogen or lower-alkyl;
R³ is lower-alkyl, aryl-lower-alkyl, heterocyclyl-lower-alkyl or lower-alkoxy-carbonyl, or, if X is not a single bond, or, if X is a single bond and m is not 0, R³ can also be hydroxy;
R⁴ is aryl or heterocyclyl;
X is a single bond, SO₂, CO, C(O)O or C(O)N(R⁵);
R⁵ is hydrogen, lower-alkyl, aryl, heterocyclyl, aryl-lower-alkyl or heterocyclyl-lower-alkyl;
m is 0, 1, 2 or 3;
n is 0 or 1;
and pharmaceutically acceptable salts and esters thereof.

2. The compound according to claim 1, having the formula (IA)

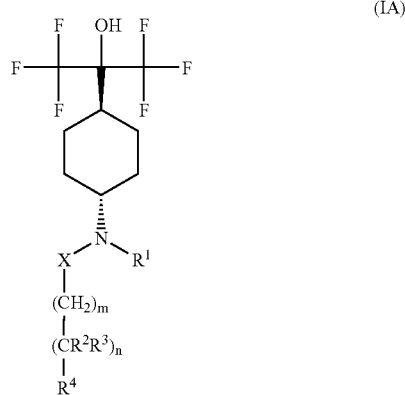

(IA)

wherein R¹, R², R³, R⁴, X, m and n are as defined in claim 1,
and pharmaceutically acceptable salts and esters thereof.

3. The compound according to claim 1, wherein R¹ is hydrogen, lower-alkyl, fluoro-lower-alkyl, lower-alkyl-carbonyl, fluoro-lower-alkyl-carbonyl, aryl-lower-alkyl, cycloalkyl-lower-alkyl or cycloalkyl-carbonyl.

4. The compound according to claim 1, wherein R¹ is fluoro-lower-alkyl, aryl-lower-alkyl or cycloalkyl-lower-alkyl.

5. The compound according to claim 1, wherein R¹ is 2,2,2-trifluoroethyl, benzyl or cyclopropylmethyl.

6. The compound according to claim 1, wherein n is 1, R² is hydrogen or lower-alkyl, and R³ is lower-alkyl, aryl-lower-alkyl or lower-alkoxy-carbonyl, or, if X is not a single bond, or, if X is a single bond and m is not 0, R³ can also be hydroxy.

7. The compound according to claim 6, wherein R² is lower-alkyl.

8. The compound according to claim 7, wherein R² is methyl.

9. The compound according to claim 6 wherein R³ is lower-alkyl.

10. The compound according to claim 9, wherein R³ is methyl.

11. The compound according to claim 1, wherein R⁴ is aryl or a heterocyclyl selected from the group consisting of thiazolyl, imidazolyl and pyrazolyl, which thiazolyl, imidazolyl or pyrazolyl is optionally substituted with 1 to 3 substituents independently selected from the group of lower-alkyl and halogen.

12. The compound according to claim 1, wherein R⁴ is aryl.

13. The compound according to claim 1, wherein R⁴ is phenyl.

14. The compound according to claim 1, wherein m is 0 or 1.

15. The compound according to claim 1, wherein m is 0.

16. The compound according to claim 15, wherein n is 0.

17. The compound according to claim 1, wherein X is a single bond, SO₂, CO or C(O)O.

18. The compound according to claim 1, wherein X is SO₂.

19. The compound according to claim 1, selected from the group consisting of
trans N-(2,2,2-Trifluoro-ethyl)-N-[4-(2,2,2-trifluoro-1-hydroxy-1-trifluoromethyl-ethyl)-cyclohexyl]-benzenesulfonamide,
trans N-[4-(2,2,2-Trifluoro-1-hydroxy-1-trifluoromethyl-ethyl)-cyclohexyl]-benzenesulfonamide,
trans N-Benzyl-2,2,2-trifluoro-N-[4-(2,2,2-trifluoro-1-hydroxy-1-trifluoromethyl-ethyl)-cyclohexyl]-acetamide,
trans Phenyl-[4-(2,2,2-trifluoro-1-hydroxy-1-trifluoromethyl-ethyl)-cyclohexylamino]-acetic acid ethyl ester,
trans N-Benzyl-N-[4-(2,2,2-trifluoro-1-hydroxy-1-trifluoromethyl-ethyl)-cyclohexyl]-acetamide,
trans N-Benzyl-N-[4-(2,2,2-trifluoro-1-hydroxy-1-trifluoromethyl-ethyl)-cyclohexyl]-benzenesulfonamide,
trans 2,4-Dimethyl-thiazole-5-sulfonic acid [4-(2,2,2-trifluoro-1-hydroxy-1-trifluoromethyl-ethyl)-cyclohexyl]-amide,
trans 1,2-Dimethyl-1H-imidazole-4-sulfonic acid [4-(2,2,2-trifluoro-1-hydroxy-1-trifluoromethyl-ethyl)-cyclohexyl]-amide,
trans 1,2-Dimethyl-1H-imidazole-4-sulfonic acid (2,2,2-trifluoro-ethyl)-[4-(2,2,2-trifluoro-1-hydroxy-1-trifluoromethyl-ethyl)-cyclohexyl]-amide,
trans 1,2-Dimethyl-1H-imidazole-4-sulfonic acid ethyl-[4-(2,2,2-trifluoro-1-hydroxy-1-trifluoromethyl-ethyl)-cyclohexyl]-amide,
trans 4-Methyl-2-propyl-thiazole-5-sulfonic acid ethyl-[4-(2,2,2-trifluoro-1-hydroxy-1-trifluoromethyl-ethyl)-cyclohexyl]-amide,
trans 2,4-Dimethyl-thiazole-5-sulfonic acid (2,2,2-trifluoro-ethyl)-[4-(2,2,2-trifluoro-1-hydroxy-1-trifluoromethyl-ethyl)-cyclohexyl]-amide,
trans 2,4-Dimethyl-thiazole-5-sulfonic acid cyclopropylmethyl-[4-(2,2,2-trifluoro-1-hydroxy-1-trifluoromethyl-ethyl)-cyclohexyl]-amide,
trans 2,4-Dimethyl-thiazole-5-sulfonic acid ethyl-[4-(2,2,2-trifluoro-1-hydroxy-1-trifluoromethyl-ethyl)-cyclohexyl]-amide,
trans N-Cyclopropylmethyl-N-[4-(2,2,2-trifluoro-1-hydroxy-1-trifluoromethyl-ethyl)-cyclohexyl]-benzenesulfonamide,
trans N-Ethyl-N-[4-(2,2,2-trifluoro-1-hydroxy-1-trifluoromethyl-ethyl)-cyclohexyl]-benzenesulfonamide,
trans 5-Chloro-1,4-dimethyl-1H-pyrazole-3-sulfonic acid (2,2,2-trifluoro-ethyl)-[4-(2,2,2-trifluoro-1-hydroxy-1-trifluoromethyl-ethyl)-cyclohexyl]-amide,
trans 5-Chloro-1,4-dimethyl-1H-pyrazole-3-sulfonic acid [4-(2,2,2-trifluoro-1-hydroxy-1-trifluoromethyl-ethyl)-cyclohexyl]-amide,
trans 2-[4-(Benzyl-ethyl-amino)-cyclohexyl]-1,1,1,3,3,3-hexafluoro-propan-2-ol,
trans 2-[4-(Benzyl-propyl-amino)-cyclohexyl]-1,1,1,3,3,3-hexafluoro-propan-2-ol,
trans 2-[4-(Benzyl-cyclopropylmethyl-amino)-cyclohexyl]-1,1,1,3,3,3-hexafluoro-propan-2-ol, trans N-Benzyl-N-[4-(2,2,2-trifluoro-1-hydroxy-1-trifluoromethyl-ethyl)-cyclohexyl]-propionamide,
trans Cyclopropanecarboxylic acid benzyl-[4-(2,2,2-trifluoro-1-hydroxy-1-trifluoromethyl-ethyl)-cyclohexyl]-amide,
trans N-Cyclopropylmethyl-N-[4-(2,2,2-trifluoro-1-hydroxy-1-trifluoromethyl-ethyl)-cyclohexyl]-benzamide,
trans N-Cyclopropylmethyl-2-phenyl-N-[4-(2,2,2-trifluoro-1-hydroxy-1-trifluoromethyl-ethyl)-cyclohexyl]-acetamide,
trans Cyclopropylmethyl-[4-(2,2,2-trifluoro-1-hydroxy-1-trifluoromethyl-ethyl)-cyclohexyl]-carbamic acid phenyl ester,
trans Cyclopropylmethyl-[4-(2,2,2-trifluoro-1-hydroxy-1-trifluoromethyl-ethyl)-cyclohexyl]-carbamic acid benzyl ester,
(rac) trans 2-{4-[cyclopropylmethyl-(2-hydroxy-2-phenyl-ethyl)-amino]-cyclohexyl}-1,1,1,3,3,3-hexafluoro-propan-2-ol,
trans Benzyl-N-[4-(2,2,2-trifluoro-1-hydroxy-1-trifluoromethyl-ethyl)-cyclohexyl]-sulfonamide,
trans Benzyl-N-(2,2,2-trifluoro-ethyl)-N-[4-(2,2,2-trifluoro-1-hydroxy-1-trifluoromethyl-ethyl)-cyclohexyl]-sulfonamide,
(rac) trans 1-Phenyl-ethanesulfonic acid (2,2,2-trifluoro-ethyl)-[4-(2,2,2-trifluoro-1-hydroxy-1-trifluoromethyl-ethyl)-cyclohexyl]-amide,
trans 2-Phenyl-propane-2-sulfonic acid (2,2,2-trifluoro-ethyl)-[4-(2,2,2-trifluoro-1-hydroxy-1-trifluoromethyl-ethyl)-cyclohexyl]-amide,
(rac) trans 1,2-diphenyl-ethanesulfonic acid (2,2,2-trifluoro-ethyl)-[4-(2,2,2-trifluoro-1-hydroxy-1-trifluoromethyl-ethyl)-cyclohexyl]-amide,
(rac) trans 3-(2-Phenyl-2-{(2,2,2-trifluoro-ethyl)-[4-(2,2,2-trifluoro-1-hydroxy-1-trifluoromethyl-ethyl)-cyclohexyl]-sulfamoyl}-ethyl)-benzoic acid methyl ester, and
cis N-Ethyl-N-[4-(2,2,2-trifluoro-1-hydroxy-1-trifluoromethyl-ethyl)-cyclohexyl]-benzenesulfonamide,
and pharmaceutically acceptable salts and esters thereof.

20. The compound according to claim 1, selected from the group consisting of
trans N-(2,2,2-Trifluoro-ethyl)-N-[4-(2,2,2-trifluoro-1-hydroxy-1-trifluoromethyl-ethyl)-cyclohexyl]-benzenesulfonamide,
trans N-Benzyl-N-[4-(2,2,2-trifluoro-1-hydroxy-1-trifluoromethyl-ethyl)-cyclohexyl]-benzenesulfonamide,
trans N-Cyclopropylmethyl-N-[4-(2,2,2-trifluoro-1-hydroxy-1-trifluoromethyl-ethyl)-cyclohexyl]-benzenesulfonamide,
trans Benzyl-N-(2,2,2-trifluoro-ethyl)-N-[4-(2,2,2-trifluoro-1-hydroxy-1-trifluoromethyl-ethyl)-cyclohexyl]-sulfonamide, and
trans 2-Phenyl-propane-2-sulfonic acid (2,2,2-trifluoro-ethyl)-[4-(2,2,2-trifluoro-1-hydroxy-1-trifluoromethyl-ethyl)-cyclohexyl]-amide,
and pharmaceutically acceptable salts and esters thereof.

21. A process for the manufacture of compounds of formula (I) as defined in claim 1, comprising the steps of
a) reacting a compound of formula (II)

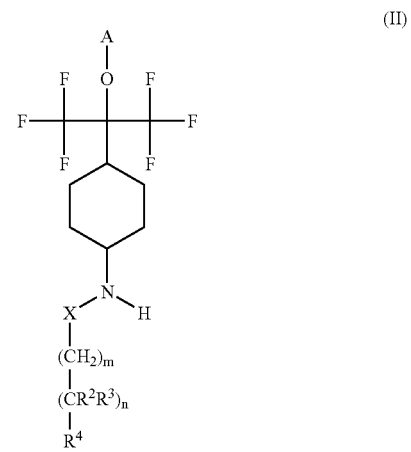

(II)

with a compound LG—$R^1$,
wherein $R^1$, $R^2$, $R^3$, $R^4$, X, m and n are as defined in any of claims 1-20, A is hydrogen or a protecting group and LG is a leaving group,
or
b) reacting a compound of formula (III)

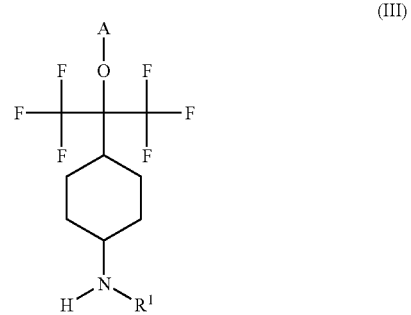

(III)

with a compound LG—X—$(CH_2)_m$—$(CR^2R^3)_n$—$R^4$,
wherein $R^1$, $R^2$, $R^3$, $R^4$, X, m and n are as defined in any of claims 1-20, A is hydrogen or a protecting group, LG is a leaving group,
and removing the protecting group A.

22. A pharmaceutical composition, comprising a therapeutically defective amount of a compound according to claim 1 and a pharmaceutically acceptable carrier and/or adjuvant.

* * * * *

UNITED STATES PATENT AND TRADEMARK OFFICE
CERTIFICATE OF CORRECTION

| | |
|---|---|
| PATENT NO. | : 7,253,282 B2 |
| APPLICATION NO. | : 11/303119 |
| DATED | : August 7, 2007 |
| INVENTOR(S) | : Henrietta Dehmlow et al. |

It is certified that error appears in the above-identified patent and that said Letters Patent is hereby corrected as shown below:

On The Title Page, Item (73) please delete "Hoffman" and insert --Hoffmann--.

In Claim 22, Column 40, Line 53, please delete "defective" and insert --effective--.

Signed and Sealed this

First Day of January, 2008

JON W. DUDAS
*Director of the United States Patent and Trademark Office*